US010769788B2

(12) United States Patent
Song et al.

(10) Patent No.: US 10,769,788 B2
(45) Date of Patent: *Sep. 8, 2020

(54) FEW-SHOT LEARNING BASED IMAGE RECOGNITION OF WHOLE SLIDE IMAGE AT TISSUE LEVEL

(71) Applicant: NantOmics, LLC, Culver City, CA (US)

(72) Inventors: Bing Song, La Canada, CA (US); Mustafa Jaber, Los Angeles, CA (US)

(73) Assignee: NantOmics, LLC, Culver City, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/129,621

(22) Filed: Sep. 12, 2018

(65) Prior Publication Data

US 2019/0080453 A1  Mar. 14, 2019

Related U.S. Application Data

(63) Continuation-in-part of application No. 15/791,209, filed on Oct. 23, 2017, now Pat. No. 10,607,343.

(Continued)

(51) Int. Cl.
  *G06T 7/00* (2017.01)
  *G06T 7/73* (2017.01)
  (Continued)

(52) U.S. Cl.
  CPC ........ *G06T 7/0014* (2013.01); *G06K 9/00147* (2013.01); *G06K 9/4628* (2013.01);
  (Continued)

(58) Field of Classification Search
  None
  See application file for complete search history.

(56) References Cited

U.S. PATENT DOCUMENTS 9,597,037 B2 * 3/2017 Gelbman ............. A61B 5/0077
10,607,343 B2 * 3/2020 Song ..................... G06T 7/0012
(Continued)

FOREIGN PATENT DOCUMENTS

WO  2015/113895 A1  8/2015
WO  2016/075096 A1  5/2016

OTHER PUBLICATIONS

Automatic detection of invasive ductal carcinoma in whole slide images with Convolutional Neural Networks Angel Cruz-Roaa,Mar. 2014 (Year: 2014).*

(Continued)

*Primary Examiner* — Nancy Bitar
(74) *Attorney, Agent, or Firm* — Mauriel Kapouytian Woods LLP; Liang Huang; Andrew Noble

(57) ABSTRACT

A computer implemented method of generating at least one shape of a region of interest in a digital image is provided. The method includes obtaining, by an image processing engine, access to a digital tissue image of a biological sample; tiling, by the image processing engine, the digital tissue image into a collection of image patches; obtaining, by the image processing engine, a plurality of features from each patch in the collection of image patches, the plurality of features defining a patch feature vector in a multidimensional feature space including the plurality of features as dimensions; determining, by the image processing engine, a user selection of a user selected subset of patches in the collection of image patches; classifying, by applying a trained classifier to patch vectors of other patches in the collection of patches, the other patches as belonging or not belonging to a same class of interest as the user selected subset of patches; and identifying one or more regions of interest based at least in part on the results of the classifying.

30 Claims, 31 Drawing Sheets
(22 of 31 Drawing Sheet(s) Filed in Color)

Related U.S. Application Data

(60) Provisional application No. 62/557,737, filed on Sep. 12, 2017.

(51) Int. Cl.

| | | |
|---|---|---|
| *G16H 10/60* | (2018.01) | |
| *G16H 80/00* | (2018.01) | |
| *G16H 10/40* | (2018.01) | |
| *G06T 7/40* | (2017.01) | |
| *G06K 9/00* | (2006.01) | |
| *G16H 30/40* | (2018.01) | |
| *G06K 9/62* | (2006.01) | |
| *G06K 9/46* | (2006.01) | |
| *G16H 50/20* | (2018.01) | |
| *G16H 40/67* | (2018.01) | |

(52) U.S. Cl.
CPC ......... *G06K 9/6215* (2013.01); *G06K 9/6269* (2013.01); *G06K 9/6274* (2013.01); *G06T 7/001* (2013.01); *G06T 7/40* (2013.01); *G06T 7/73* (2017.01); *G16H 10/40* (2018.01); *G16H 10/60* (2018.01); *G16H 30/40* (2018.01); *G16H 40/67* (2018.01); *G16H 50/20* (2018.01); *G16H 80/00* (2018.01); *G06T 2207/20021* (2013.01); *G06T 2207/20081* (2013.01); *G06T 2207/20084* (2013.01); *G06T 2207/30004* (2013.01); *G06T 2207/30024* (2013.01); *G06T 2207/30096* (2013.01)

(56) References Cited

U.S. PATENT DOCUMENTS

| | | | | |
|---|---|---|---|---|
| 2002/0186875 | A1* | 12/2002 | Burmer | G06K 9/00127 382/133 |
| 2004/0093166 | A1* | 5/2004 | Kil | G01N 1/06 702/19 |
| 2009/0116737 | A1 | 5/2009 | Kiraly et al. | |
| 2009/0262993 | A1* | 10/2009 | Kotsianti | G06K 9/00127 382/128 |
| 2012/0147189 | A1* | 6/2012 | Zhang | G06K 9/00791 348/149 |
| 2015/0110381 | A1* | 4/2015 | Parvin | G06K 9/6249 382/133 |
| 2015/0213302 | A1* | 7/2015 | Madabhushi | G06K 9/00147 382/133 |
| 2016/0110584 | A1 | 4/2016 | Remiszewski et al. | |
| 2018/0070905 | A1* | 3/2018 | El-Baz | G06T 7/0016 |
| 2018/0114317 | A1 | 4/2018 | Song et al. | |

OTHER PUBLICATIONS

Comparison of One-Class SVM and Two-Class SVM for Fold Recognition Alexander Senf, Xue-wen Chen, and Anne Zhang The University of Kansas (Year: 2006).*

Rich feature hierarchies for accurate object detection and semantic segmentation Tech report (v5) Ross Girshick Jeff Donahue Trevor Darrell Jitendra Malik UC Berkeley (Year: 2014).*

The International Search Report and Written Opinion issued in International Application No. PCT/US2018/050737 dated Jan. 18, 2019, 13 pages.

Girshick et al., "Rich feature hierarchies for accurate object detection and semantic segmentation," Proceedings of the IEEE conference on computer vision and pattern recognition, 2014, 8 pages.

Senf et al., "Comparison of One-Class SVM and Two-Class SVM for Fold Recognition," International Conference on Neural Information Processing, 2006, 10 pages.

International Search Report and Written Opinion issued in International Application No. PCT/US2017/057925 dated Feb. 6, 2018, 12 pages.

Xu et al., "Efficient Lung Cancer Cell Detection with Deep Convolution Neural Network," International Workshop on Patch-based Techniques in Medical Imaging, 2015, pp. 79-86.

Pan et al., "An Effective Approach for Robust Lung Cancer Cell Detection," International Workshop on Patch-based Techniques in Medical Imaging, 2015, pp. 87-94.

Li et al., "Fast Regions-of-Interest Detection in Whole Slide Histopathology Images," International Workshop on Patch-based Techniques in Medical Imaging, 2015, pp. 120-127.

Yao et al., "Computer-Assisted Diagnosis of Lung Cancer Using Quantitative Topology Features," International Workshop on Machine Learning in Medical Imaging, 2015, pp. 288-295.

Jiang et al., "Joint Kernel-Based Supervised Hashing for Scalable Histopathological Image Analysis," International Conference on Medical Image Computing and Computer-Assisted Intervention, 2015, pp. 366-373.

Cruz-Roa et al., "Automatic detection of invasive ductal carcinoma in whole slide images with Convolutional Neural Networks," Medical Imaging 2014: Digital Pathology, vol. 9041, 15 pages.

Huang, "Imaging Genomics Based Lung Cancer Clinical Outcome Prediction," http://ranger.uta.edu/~huang/R_Lung.htm, downloaded on Sep. 8, 2016, 2 pages.

"Cell Detection Demo," https://celldetection.zhengxu.work/, downloaded on Sep. 8, 2016, 1 page.

Szegedy et al., "Rethinking the Inception Architecture for Computer Vision," Proceedings of the IEEE Conference on Computer Vision and Pattern Recognition, 2016, 10 pages.

Krahenbuhl et al., "Efficient Inference in Fully Connected CRFs with Gaussian Edge Potentials," NIPS, 9 pages.

Long et al., "Fully Convolutional Networks for Semantic Segmentation," Proceedings of the IEEE Conference on Computer Vision and Pattern Recognition, 2015, pp. 3431-3440.

Extended European Search Report issued in European Application No. 17862640.4 dated Apr. 3, 2020, 10 pages.

Krahenbuhl et al., "Efficient Inference in Fully Connected CRFs with Gaussian Edge Potentials," Advances in Neural Information Processing Systems, 2011, http://papers.nips.cc/paper/4296-efficient-inference-in-fully-connected-crfs-with-gaussian-edge-potentials.pdf, 9 pages.

Office Action issued in Canadian Application No. 3,040,518 dated May 21, 2020, 6 pages.

* cited by examiner

| type | patch size/stride or remarks | input size |
|---|---|---|
| conv | 3×3/2 | 299×299×3 |
| conv | 3×3/1 | 149×149×32 |
| conv padded | 3×3/1 | 147×147×32 |
| pool | 3×3/2 | 147×147×64 |
| conv | 3×3/1 | 73×73×64 |
| conv | 3×3/2 | 71×71×80 |
| conv | 3×3/1 | 35×35×192 |
| 3×Inception | As in figure 5 | 35×35×288 |
| 5×Inception | As in figure 6 | 17×17×768 |
| 2×Inception | As in figure 7 | 8×8×1280 |
| pool | 8 × 8 | 8 × 8 × 2048 |
| linear | logits | 1 × 1 × 2048 |
| softmax | classifier | 1 × 1 × 1000 |

*Figures 5, 6 and 7 refer to
"Rethinking the Inception Architecture for Computer Vision"
by Szegedy

The following two buttons are in the middle-right areas.

Save DB button will save all of the positive/negative samples (not limited to that in the current slide) to the hard disk. You can reuse these training data after you login next time. If you do not save it, the data will lost when you login next time.
Erase DB button will erase everything in the database as well as the samples that you selected but not saved yet.

*How to Select Samples*
1. Using Positive/negative selector to decide the type of sample you want to select.
2. Move the mouse to the area that you want to select. You can click the mouse button to zoom in.
3. Press s key and drag the mouse in the area that you want to select. You will see yellow box for positive or blue box for negative are displayed on the screen.

*How to Delete Samples*
To delete the samples, move the mouse inside the patch box and press d key. The box will disappear after you delete it.

Upload files
Drag and drop whole slide images (WSI) files to the dashed box and click Upload Button. The files will upload to your designed image root directory. It may take several minutes to upload one WSI file.

WSI Directory input box allows you to upload the files to the sub folder in your account. It will create a new folder as needed.

Since the Safari browser cannot upload the file if the file size is bigger than 0.5GB, please use Chrome or Explore instead.

Since the backend system is not up yet, please contact hing.song@manatomics.com to build meta data for the WSI that you want to analysis.

Manage Database
That page allows you use multiple databases. If this is the first time that you enter this page, you are using default database. You can add, delete, or set default database in this page.

*Add database*
1. Enter a database name in the new_database_name input box.
2. Click Add button, a new database will appear on the database list.

*Set default database*
1. Select one check box from the database list
2. Click Set button.

*Delete databases*
1. Select the checkboxes of the database that you want to delete
2. Click Delete button

FIG. 11C

FEW-SHOT LEARNING BASED IMAGE RECOGNITION OF WHOLE SLIDE IMAGE AT TISSUE LEVEL

CROSS-REFERENCE TO RELATED APPLICATIONS

This application claims priority to U.S. Provisional Application No. 62/557,737, filed Sep. 12, 2017, is a continuation-in-part of U.S. application Ser. No. 15/791,209, filed Oct. 23, 2017, and is related to U.S. Provisional Application No. 62/411,290, filed Oct. 21, 2016, each filed before the United States Patent and Trademark Office. The above applications, and all other documents referenced in this application, are incorporated herein by reference in their entirety.

INTRODUCTION

The present technology relates generally to recognition, and for some embodiments, to image recognition. In some embodiments, the technology relates to histopathology, the microscopic examination of tissue for the purpose of determining whether the tissue is diseased and/or studying diseased tissue. The tissue may be removed from any part of the body including, for example, breast lumps, specimens of bowel, kidney, liver, uterus lining, lung, chest, lymph node, muscle, nerve, skin, testicle, thyroid, or the like.

In some embodiments, this disclosed technology relates to identifying regions of interest within a digital image, for example, identifying foreground objects from background scenes, or identifying cancer cells within a digital histopathology image. The types of cancer in the cancer cells may include, but are not necessarily limited to, breast cancer, bladder cancer, brain cancer, lung cancer, pancreatic cancer, skin cancer, colorectal cancer, prostate cancer, stomach cancer, liver cancer, cervical cancer, esophageal cancer, leukemia, non-hodgkin lymphoma, kidney cancer, uterine cancer, bile duct cancer, bone cancer, ovarian cancer, gallbladder cancer, gastrointestinal cancer, oral cancer, throat cancer, ocular cancer, pelvic cancer, spinal cancer, testicular cancer, vaginal cancer, vulvar cancer, and thyroid cancer. The regions of interest/classes of interest may also be broader and include abnormal tissue, benign tissue, malignant tissue, bone tissue, skin tissue, nerve tissue, interstitial tissue, muscle tissue, connective tissue, scar tissue, lymphoid tissue, fat, epithelial tissue, nervous tissue, and blood vessels.

The tissue may be collected from a subject in multiple settings including biopsy, surgery, or autopsy. After tissues are removed from the subject, they are prepared for chemical fixation by being placed in a fixative such as formalin to prevent decay of the tissue. The tissues are then either frozen or set in molten wax. Sections of the tissues are then cut and placed on slides Once the tissue sections are on slides, a pathologist views the slides through a microscope to determine whether the tissue is, for example, diseased and, if diseased, determine the stage of the disease. For example, a pathologist may determine whether a breast lump includes breast cancer cells and, if it does, a pathologist may determine the grade and/or stage of cancer. Pathologists may also make determinations regarding tissue other than whether it is diseased. For example, a pathologist may determine whether tissue includes lymphocytes. However, there is a technical problem with these determinations in that they are often unreliable, expensive, time consuming, and generally require verification by multiple pathologists to minimize the likelihood of false determinations.

One solution to this technical problem is to use computer vision to determine a tissue characteristic, such as the type and/or grade of cancer by training a neural network (or other machine learning system) to determine whether a digital image of tissue is diseased and determine the type (e.g., breast cancer) and stage (e.g., stage 3) of the disease. However, there is a technical problem with this approach in that, for example, it requires a lot of training data for each disease (e.g., a large amount of positive and negative training patches of various cancers would be required).

Some embodiments of the present invention solve the above technical problem and provide a technical solution of using neural networks and, more specifically, convolutional neural networks, and support vector machines, in combination with limited input, such as from a pathologist or other person or entity, to determine whether tissue is likely to be diseased.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4B illustrates layers of a convolutional neural network that can implement one or more aspects of an embodiment of the invention;

FIG. 10A illustrates a representation of positive patches, following analysis by the two-class SVM, to one or more aspects of an embodiment of the invention;

FIGS. 11A-11I illustrate slide images shown on a graphical user interface generated by an electronic device that implements one or more aspects of an embodiment of the invention.

While the invention is described with reference to the above drawings, the drawings are intended to be illustrative, and the invention contemplates other embodiments within the spirit of the invention.

DETAILED DESCRIPTION OF EMBODIMENTS OF THE PRESENT INVENTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

Figure 1:
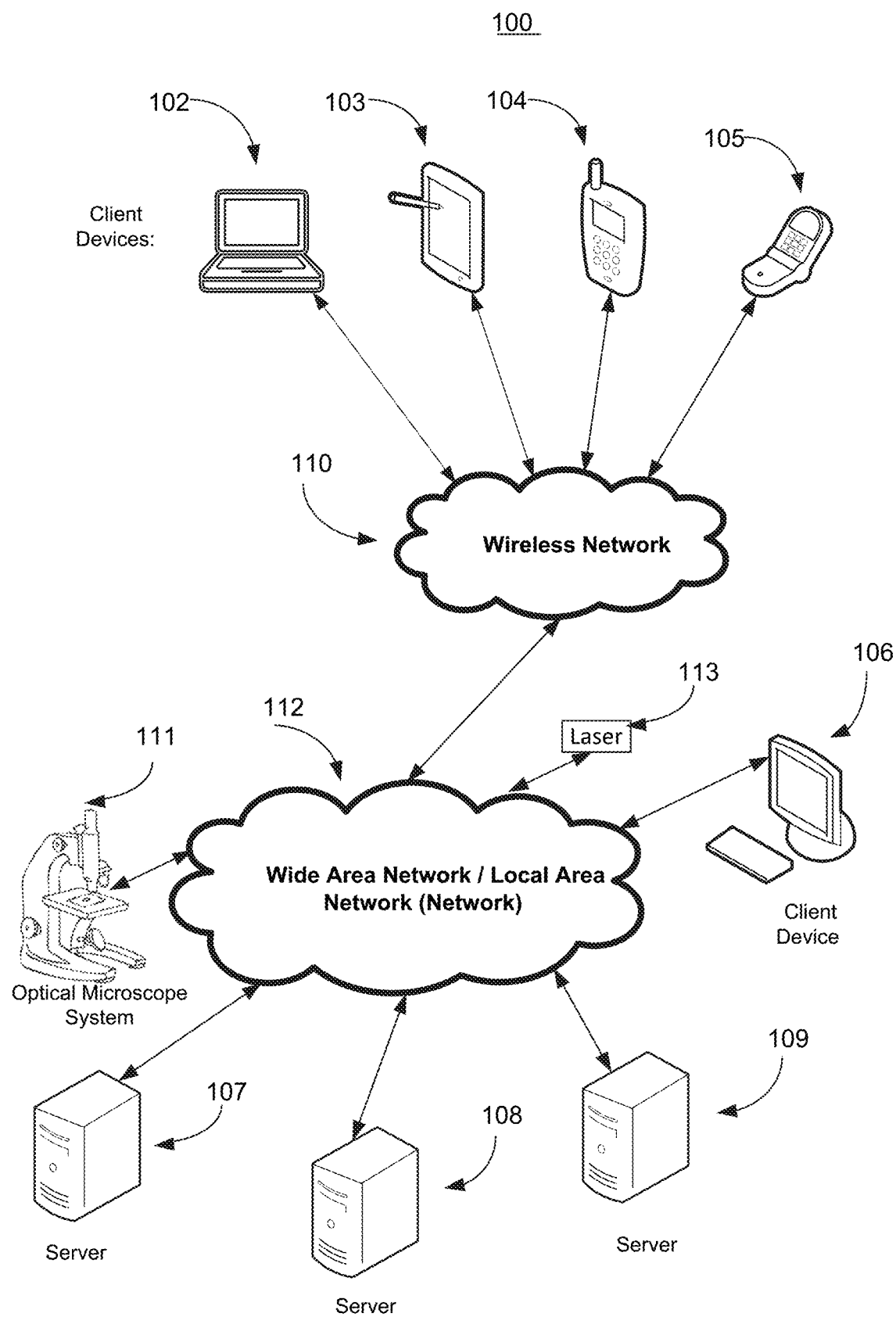
FIG. 1 illustrates a block diagram of a distributed computer system that can implement one or more aspects of an embodiment of the present invention.

FIG. 1 illustrates components of one embodiment of an environment in which the invention may be practiced. Not all of the components may be required to practice the invention, and variations in the arrangement and type of the components may be made without departing from the spirit or scope of the invention. As shown, the system 100 includes one or more Local Area Networks ("LANs")/Wide Area Networks ("WANs") 112, one or more wireless networks 110, one or more wired or wireless client devices 106, mobile or other wireless client devices 102-106, servers 107-109, optical microscope system 111, laser 113, and may include or communicate with one or more data stores or databases. Various of the client devices 102-106 may include, for example, desktop computers, laptop computers, set top boxes, tablets, cell phones, smart phones, and the like. The servers 107-109 can include, for example, one or more application servers, content servers, search servers, web servers, Graphics Processing Unit (GPU) servers, and the like.

Figure 2:
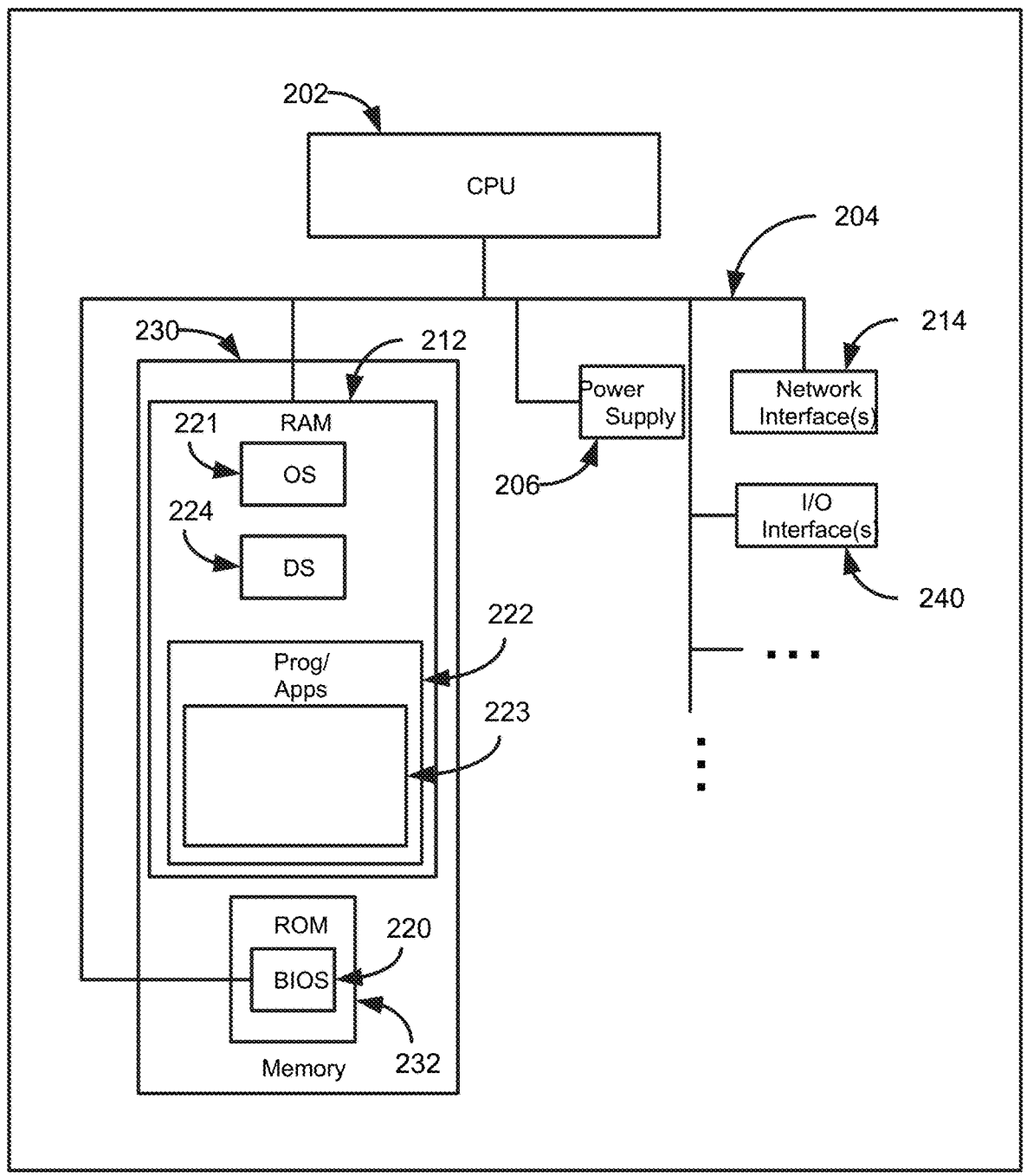
FIG. 2 illustrates a block diagram of an electronic device that can implement one or more aspects of an embodiment of the invention.

Optical microscope system 111 may include a microscope, an ocular assembly, a camera, a slide platform, as well as components of electronic device 200 as shown in FIG. 2. Although FIG. 1 shows optical microscope system 111 being communicatively coupled to network 112, it may also be coupled to any or all of servers 107-109, wireless network 110, and/or any of client devices 102-106.

Laser 113, which may be connected to network 112, may be used for cutting a portion of tissue believed to have cancer cells (or other types of cells).

FIG. 2 illustrates a block diagram of an electronic device 200 that can implement one or more aspects of systems and methods for interactive video generation and rendering according to one embodiment of the invention. Instances of the electronic device 200 may include servers, e.g., servers 107-109, optical microscope system 111, and client devices, e.g., client devices 102-106. In general, the electronic device 200 can include a processor/CPU 202, memory 230, a power supply 206, and input/output (I/O) components/devices 240, e.g., microphones, speakers, displays, smartphone displays, touchscreens, keyboards, mice, keypads, GPS components, etc., which may be operable, for example, to provide graphical user interfaces.

A user may provide input via a touchscreen of an electronic device 200. A touchscreen may determine whether a user is providing input by, for example, determining whether the user is touching the touchscreen with a part of the user's body such as his or her fingers. The electronic device 200 can also include a communications bus 204 that connects the aforementioned elements of the electronic device 200. Network interfaces 214 can include a receiver and a transmitter (or transceiver), and one or more antennas for wireless communications.

The processor 202 can include one or more of any type of processing device, e.g., a Central Processing Unit (CPU). Also, for example, the processor can be central processing logic or other logic, may include hardware, firmware, software, or combinations thereof, to perform one or more functions or actions, or to cause one or more functions or actions from one or more other components. Also, based on a desired application or need, central processing logic, or other logic, may include, for example, a software controlled microprocessor, discrete logic, e.g., an Application Specific Integrated Circuit (ASIC), a programmable/programmed logic device, memory device containing instructions, etc., or combinatorial logic embodied in hardware. Furthermore, logic may also be fully embodied as software. Electronic device 200 may also include a GPU (not shown), a specialized electronic circuit designed to manipulate and alter memory to accelerate the creation and processing of images in a frame buffer intended for output to a display device.

The memory 230, which can include Random Access Memory (RAM) 212 and Read Only Memory (ROM) 232, can be enabled by one or more of any type of memory device, e.g., a primary (directly accessible by the CPU) or secondary (indirectly accessible by the CPU) storage device (e.g., flash memory, magnetic disk, optical disk, and the like). The RAM can include an operating system 221, data storage 224, which may include one or more databases, and programs and/or applications 222, which can include, for example, software aspects of the digital histopathology and microdissection program 223. The ROM 232 can also include Basic Input/Output System (BIOS) 220 of the electronic device.

The program 223 is intended to broadly include or represent all programming, applications, algorithms, software and other tools necessary to implement or facilitate methods and systems according to embodiments of the invention. The elements of systems and methods for interactive video generation and rendering program may exist on a single server computer or be distributed among multiple computers, servers, devices or entities, which can include advertisers, publishers, data providers, etc. If the systems and methods for interactive video generation and rendering program is distributed among multiple computers, servers, devices or entities, such multiple computers would communicate, for example, as shown on FIG. 1.

The power supply 206 contains one or more power components, and facilitates supply and management of power to the electronic device 200.

The input/output components, including Input/Output (I/O) interfaces 240, can include, for example, any interfaces for facilitating communication between any components of the electronic device 200, components of external devices (e.g., components of other devices of the network or system 100), and end users. For example, such components can include a network card that may be an integration of a receiver, a transmitter, a transceiver, and one or more input/output interfaces. A network card, for example, can facilitate wired or wireless communication with other devices of a network. In cases of wireless communication, an antenna can facilitate such communication. Also, some of the input/output interfaces 240 and the bus 204 can facilitate communication between components of the electronic device 200, and in an example can ease processing performed by the processor 202.

Where the electronic device 200 is a server, it can include a computing device that can be capable of sending or receiving signals, e.g., via a wired or wireless network, or may be capable of processing or storing signals, e.g., in memory as physical memory states. The server may be an application server that includes a configuration to provide one or more applications, e.g., aspects of the systems and methods for interactive video generation and rendering, via a network to another device. Also, an application server may, for example, host a Web site that can provide a user interface for administration of example aspects of the systems and methods for interactive video generation and rendering.

Any computing device capable of sending, receiving, and processing data over a wired and/or a wireless network may act as a server, such as in facilitating aspects of implementations of the systems and methods for interactive video generation and rendering. Thus, devices acting as a server may include devices such as dedicated rack-mounted servers, desktop computers, laptop computers, set top boxes, integrated devices combining one or more of the preceding devices, and the like.

Servers may vary widely in configuration and capabilities, but they generally include one or more central processing units, memory, mass data storage, a power supply, wired or wireless network interfaces, input/output interfaces, and an operating system such as Windows Server, Mac OS X, Unix, Linux, FreeBSD, and the like.

A server may include, for example, a device that is configured, or includes a configuration, to provide data or content via one or more networks to another device, such as in facilitating aspects of an example systems and methods for interactive video generation and rendering. One or more servers may, for example, be used in hosting a Web site, such as the web site www.microsoft.com. One or more servers may host a variety of sites, such as, for example, business sites, informational sites, social networking sites, educational sites, wikis, financial sites, government sites, personal sites, and the like.

Servers may also, for example, provide a variety of services, such as Web services, third-party services, audio services, video services, email services, HTTP or HTTPS services, Instant Messaging (IM) services, Short Message Service (SMS) services, Multimedia Messaging Service (MMS) services, File Transfer Protocol (FTP) services, Voice Over IP (VOIP) services, calendaring services, phone services, and the like, all of which may work in conjunction with example aspects of an example systems and methods for interactive video generation and rendering. Content may include, for example, text, images, audio, video, and the like.

In example aspects of the systems and methods for interactive video generation and rendering, client devices may include, for example, any computing device capable of sending and receiving data over a wired and/or a wireless network. Such client devices may include desktop computers as well as portable devices such as cellular telephones, smart phones, display pagers, Radio Frequency (RF) devices, Infrared (IR) devices, Personal Digital Assistants (PDAs), handheld computers, GPS-enabled devices tablet computers, sensor-equipped devices, laptop computers, set top boxes, wearable computers, integrated devices combining one or more of the preceding devices, and the like.

Client devices, as may be used in example systems and methods for interactive video generation and rendering, may range widely in terms of capabilities and features. For example, a cell phone, smart phone or tablet may have a numeric keypad and a few lines of monochrome Liquid-Crystal Display (LCD) display on which only text may be displayed. In another example, a Web-enabled client device may have a physical or virtual keyboard, data storage (such as flash memory or SD cards), accelerometers, gyroscopes, GPS or other location-aware capability, and a 2D or 3D touch-sensitive color screen on which both text and graphics may be displayed.

Client devices, such as client devices 102-106, for example, as may be used in example systems and methods for interactive video generation and rendering, may run a variety of operating systems, including personal computer operating systems such as Windows, iOS or Linux, and mobile operating systems such as iOS, Android, Windows Mobile, and the like.

Client devices may be used to run one or more applications that are configured to send or receive data from another computing device. Client applications may provide and receive textual content, multimedia information, and the like. Client applications may perform actions such as browsing webpages, using a web search engine, interacting with various apps stored on a smart phone, sending and receiving messages via email, SMS, or MMS, playing games (such as fantasy sports leagues), receiving advertising, watching locally stored or streamed video, or participating in social networks.

In example aspects of the systems and methods for interactive video generation and rendering, one or more networks, such as networks 110 or 112, for example, may couple servers and client devices with other computing devices, including through wireless network to client devices. A network may be enabled to employ any form of computer readable media for communicating information from one electronic device to another. A network may include the Internet in addition to Local Area Networks (LANs), Wide Area Networks (WANs), direct connections, such as through a Universal Serial Bus (USB) port, other forms of computer-readable media, or any combination thereof. On an interconnected set of LANs, including those based on differing architectures and protocols, a router acts as a link between LANs, enabling data to be sent from one to another.

Communication links within LANs may include twisted wire pair or coaxial cable, while communication links between networks may utilize analog telephone lines, cable lines, optical lines, full or fractional dedicated digital lines including T1, T2, T3, and T4, Integrated Services Digital Networks (ISDNs), Digital Subscriber Lines (DSLs), wireless links including satellite links, optic fiber links, or other communications links known to those skilled in the art. Furthermore, remote computers and other related electronic devices could be remotely connected to either LANs or WANs via a modem and a telephone link.

A wireless network, such as wireless network 110, as in example systems and methods for interactive video generation and rendering, may couple devices with a network. A wireless network may employ stand-alone ad-hoc networks, mesh networks, Wireless LAN (WLAN) networks, cellular networks, and the like.

A wireless network may further include an autonomous system of terminals, gateways, routers, or the like connected by wireless radio links, or the like. These connectors may be configured to move freely and randomly and organize themselves arbitrarily, such that the topology of wireless network may change rapidly. A wireless network may further employ a plurality of access technologies including 2nd (2G), 3rd (3G), 4th (4G) generation, Long Term Evolution (LTE) radio access for cellular systems, WLAN, Wireless Router (WR) mesh, and the like. Access technologies such as 2G, 2.5G, 3G, 4G, and future access networks may enable wide area coverage for client devices, such as client devices with various degrees of mobility. For example, a wireless network may enable a radio connection through a radio network access technology such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, and the like. A wireless network may include virtually any wireless communication mechanism by which information may travel between client devices and another computing device, network, and the like.

Internet Protocol (IP) may be used for transmitting data communication packets over a network of participating digital communication networks, and may include protocols such as TCP/IP, UDP, DECnet, NetBEUI, IPX, Appletalk, and the like. Versions of the Internet Protocol include IPv4 and IPv6. The Internet includes local area networks (LANs), Wide Area Networks (WANs), wireless networks, and long haul public networks that may allow packets to be communicated between the local area networks. The packets may be transmitted between nodes in the network to sites each of which has a unique local network address. A data communication packet may be sent through the Internet from a user site via an access node connected to the Internet. The packet may be forwarded through the network nodes to any target site connected to the network provided that the site address of the target site is included in a header of the packet. Each packet communicated over the Internet may be routed via a path determined by gateways and servers that switch the packet according to the target address and the availability of a network path to connect to the target site.

The header of the packet may include, for example, the source port (16 bits), destination port (16 bits), sequence number (32 bits), acknowledgement number (32 bits), data offset (4 bits), reserved (6 bits), checksum (16 bits), urgent pointer (16 bits), options (variable number of bits in multiple of 8 bits in length), padding (may be composed of all zeros and includes a number of bits such that the header ends on a 32 bit boundary). The number of bits for each of the above may also be higher or lower.

A "content delivery network" or "content distribution network" (CDN), as may be used in example systems and methods for interactive video generation and rendering, generally refers to a distributed computer system that comprises a collection of autonomous computers linked by a network or networks, together with the software, systems, protocols and techniques designed to facilitate various services, such as the storage, caching, or transmission of content, streaming media and applications on behalf of content providers. Such services may make use of ancillary technologies including, but not limited to, "cloud computing," distributed storage, DNS request handling, provisioning, data monitoring and reporting, content targeting, personalization, and business intelligence. A CDN may also enable an entity to operate and/or manage a third party's Web site infrastructure, in whole or in part, on the third party's behalf.

A Peer-to-Peer (or P2P) computer network relies primarily on the computing power and bandwidth of the participants in the network rather than concentrating it in a given set of dedicated servers. P2P networks are typically used for connecting nodes via largely ad hoc connections. A pure peer-to-peer network does not have a notion of clients or servers, but only equal peer nodes that simultaneously function as both "clients" and "servers" to the other nodes on the network.

One embodiment of the present invention includes systems, methods, and a non-transitory computer readable storage medium or media tangibly storing computer program logic capable of being executed by a computer processor, related to digital histopathology and microdissection.

As mentioned above, methods that rely entirely on various pathologists to review and make determinations as to whether a tissue sample ("sample") has a certain characteristic such as being diseased or, in particular, diseased with cancer can be unreliable, expensive, or time consuming. On the other hand, if the determination is made solely by a neural network, a large amount of training data may be necessary for each of the various tissue characteristics such as types and grades of diseases (including both positive and negative training data), which is difficult to collect. For example, generating such training data may require receiving input from one or more pathologists for a large number of images as to whether such images are positive or negative for a particular disease or other characteristic of an image of a sample.

An embodiment of the present invention includes determining whether a sample is diseased. The embodiment described below refers, in particular, to cancer. However, embodiments of the present invention may be used to make a determination as to other characteristics of a sample. For example, embodiments of the present invention may be used to determine whether a sample shows other diseases or grades of diseases. As another example, embodiments of the present invention may be used to determine whether a sample includes lymphocytes.

An embodiment of the present invention relates to determining whether a sample is cancerous by using computer vision and input from one or more pathologists as to whether one or more patches of an image are positive or negative for a particular type or grade of cancer. Other embodiments relate to recognizing whether a sample (e.g., image, sound, pattern, etc.) is positive or negative for satisfying a criteria (e.g., criteria for recognizing a person, object, sound, pattern, etc.).

Computer vision relates to the automated extraction, analysis and understanding of useful information from one or more digital images. For example, computer vision may be used to determine the age of a person in a photograph by determining the location of a face of the person in a digital image, determining the location of the eyes of such person, and measuring the interpupillary distance of such person.

In the field of machine learning, a Convolutional Neural Network ("CNN") is an artificial neural network which may be used in the field of computer vision. The article Rethinking the Inception Architecture for Computer Vision by Christian Szegedy et al. (arXiv:1512.00567v3 [cs.CV] 11 Dec. 2015) discusses the use of CNNs in computer vision and is incorporated by reference herein in its entirety.

Figure 3:
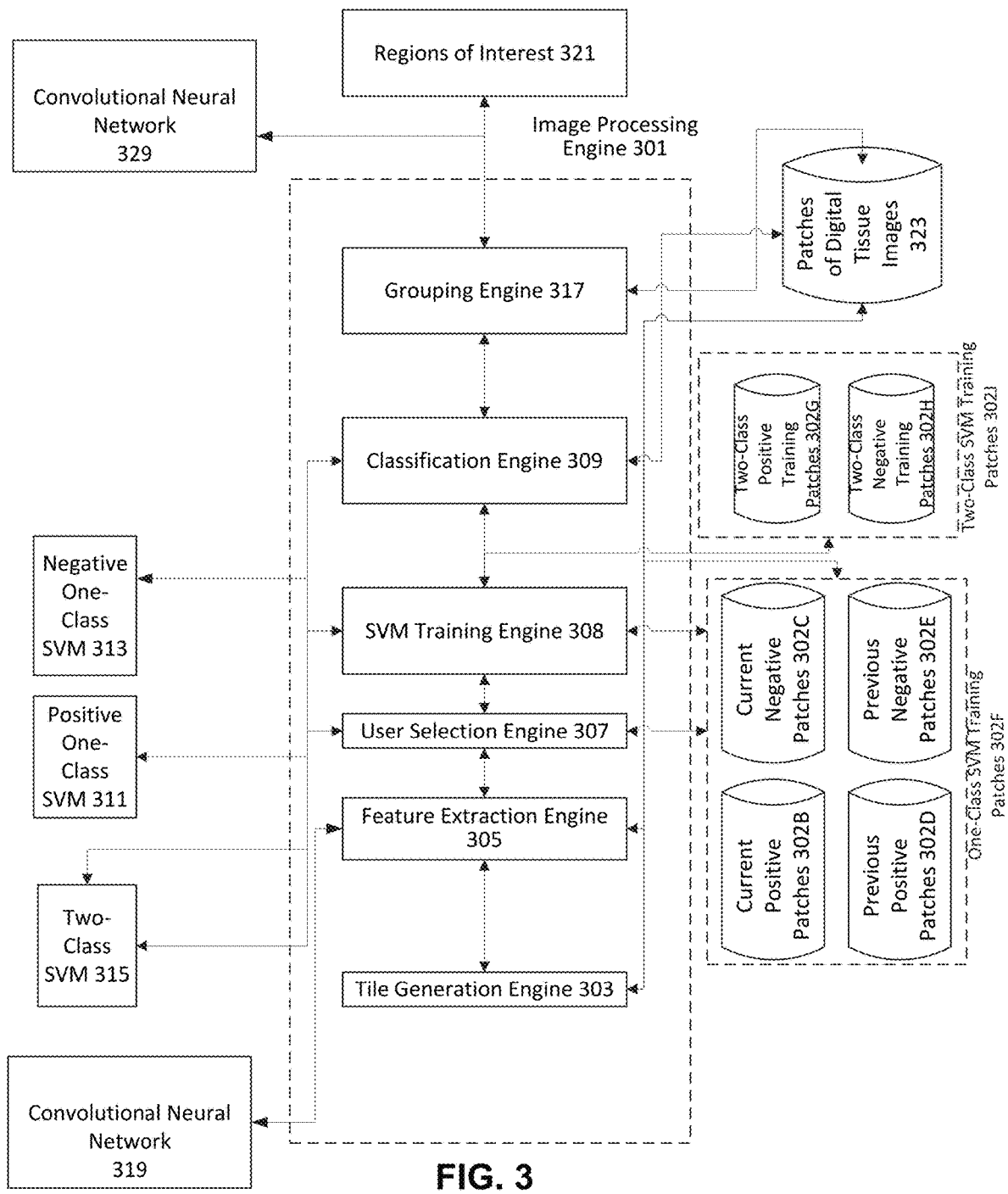
FIG. 3 illustrates an architecture diagram of an electronic device that can implement one or more aspects of an embodiment of the invention.

FIG. 3 illustrates an architecture diagram of an electronic device that can implement one or more aspects of an embodiment of the invention. FIG. 3 includes image processing engine 301 which processes digital images to output regions of interest 321. Image processing engine 301 includes tile generation engine 303, feature extraction engine 305, user selection engine 307, SVM Training Engine 308, classification engine 309, and grouping engine 317. Image processing engine 301 is coupled to (e.g., in communication with) CNN 319, digital tissue images database 323, training patches databases 302F and 302J, positive one-class Support Vector Machine (SVM) 311, negative one-class SVM 313, and two-class SVM 315. Image processing engine 301 is also coupled to CNN 329, which can utilize the output of image processing engine 301 as training data to train CNN 329 to classify other digital images.

Figure 4A:
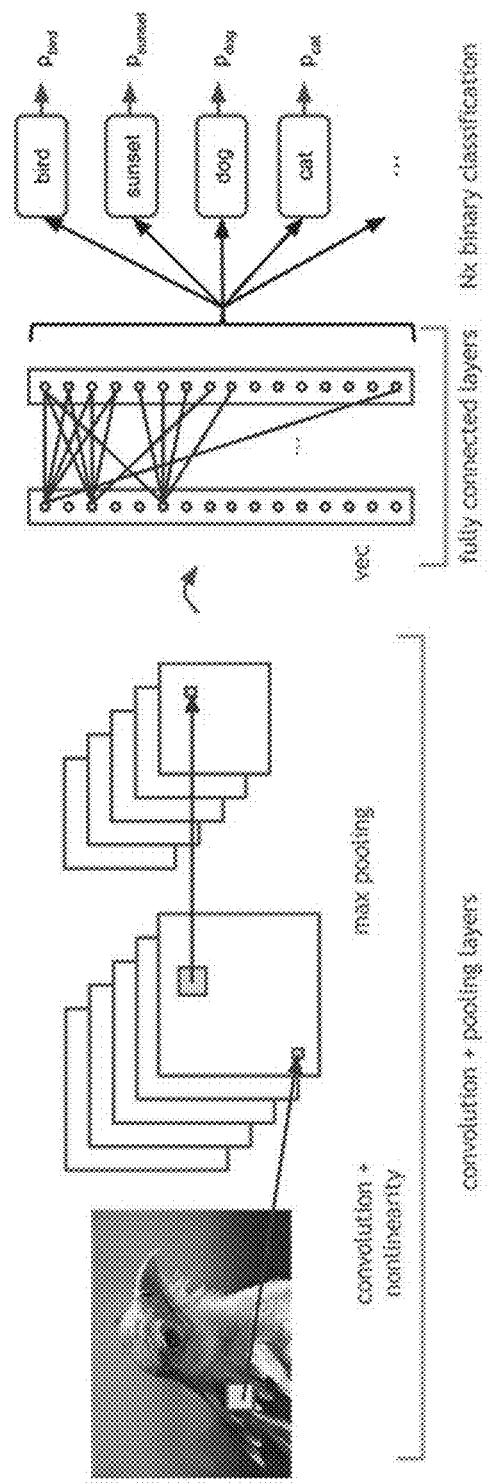
FIG. 4A illustrates a general deep learning architecture that can implement one or more aspects of an embodiment of the invention.

FIG. 4A shows a deep learning architecture of a CNN. The CNN has a plurality of layers, as shown in FIG. 4B, and a plurality of parameters in each layer (input size). FIG. 4B includes information on the type of layer, the patch size, and the input size of each layer. The values of the parameters determine the output of the CNN.

The CNN 319 may be provided an input of an image of a tissue sample (or a patch of such an image) and the CNN 319 may provide, as an output, a plurality of (for example, 2048) image feature values (i.e., feature extraction or feature representation of visual descriptors). Such output would be from the linear layer. The softmax layer, shown directly below the linear layer in FIG. 4B, may not need to be used and may be removed from the architecture of CNN 319. The image of the tissue sample may be a slide image and, in particular, a digital histopathology image.

Figure 4C:
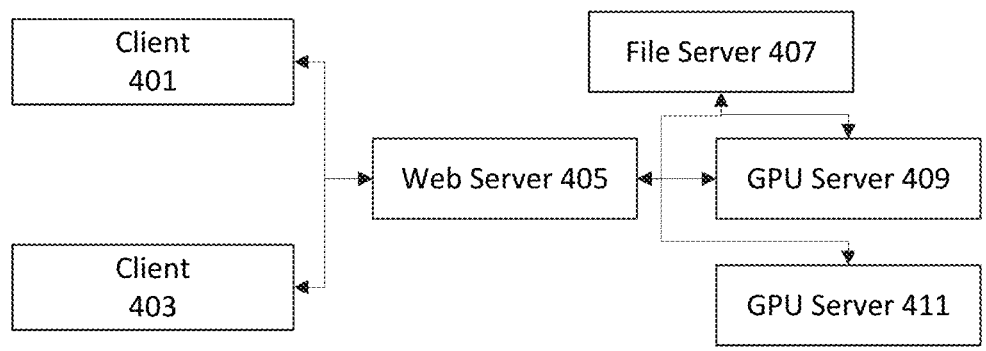
FIG. 4C illustrates a hardware architecture diagram of devices that can implement one or more aspects of an embodiment of the invention.
Figure 5A:
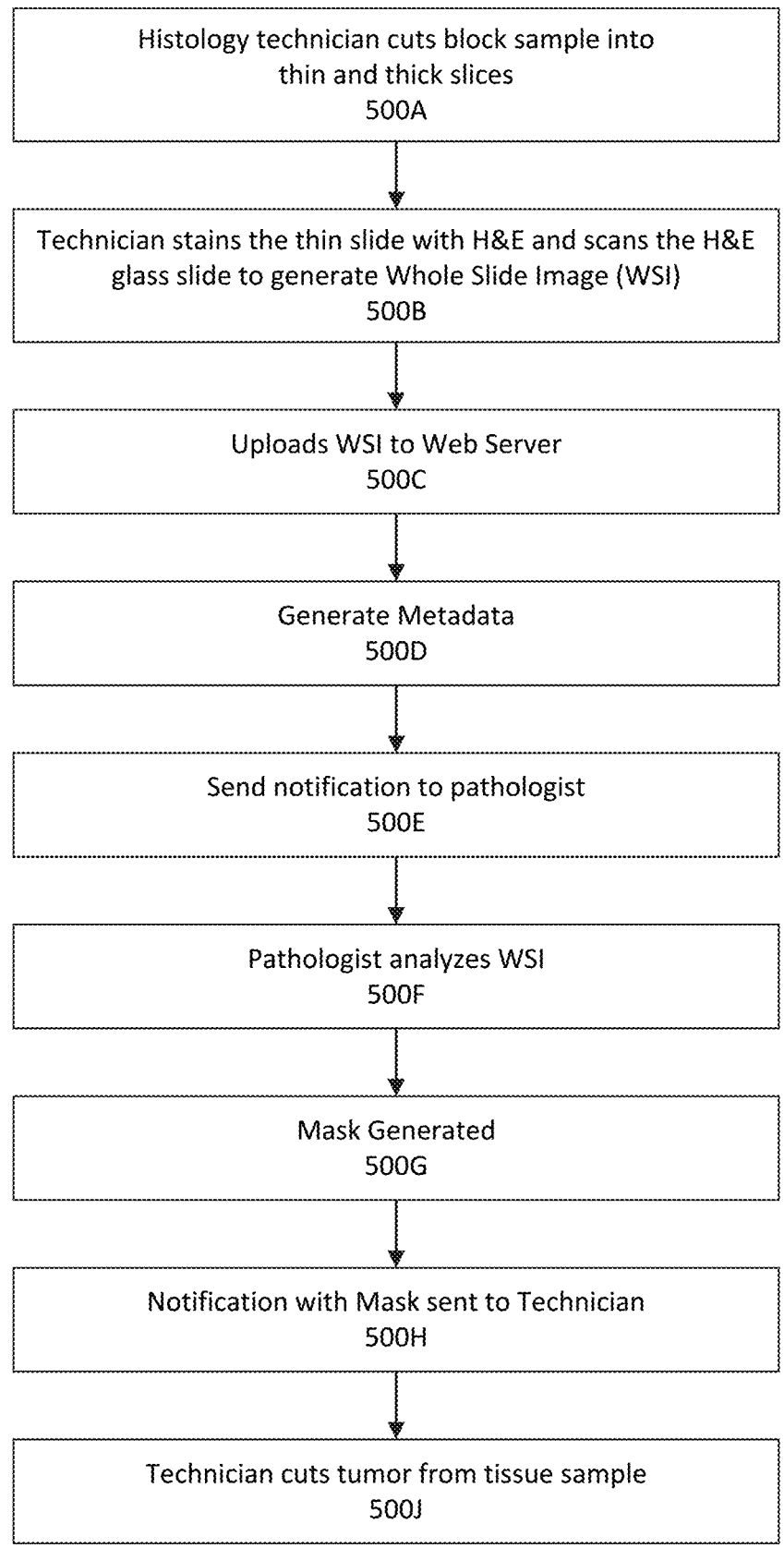
FIGS. 5A-5D illustrate a process carried out by an electronic device that can implement one or more aspects of an embodiment of the invention.

FIG. 5A illustrates a process carried out by an electronic device that can implement one or more aspects of an embodiment of the invention. More specifically, FIG. 5A shows an end-to-end high level process beginning with a histology technician cutting a tissue sample into slices and ending with the technician cutting a portion of the sample determined by the system to be cancerous (or another disease) from the sample. Reference will be made to the hardware architecture diagram shown in FIG. 4C. It should be understood that FIG. 4C omits certain hardware for simplicity. For example, FIG. 4C does not show networks, switches, routers, and the like. However, one of ordinary skill in the art would understand that clients are connected to servers or other clients via networks and servers are connected to servers via networks. That is, for example, clients 401 and 403 of FIG. 4C may be any of client devices 102-106, optical microscope system 111, or laser 113 of FIG. 1, and servers 405, 407, 409, and 411 of FIG. 4C may be servers 107-109 of FIG. 1. In the alternative, any of the processing described below may take place on any other device (for example, processing that takes place on a web server may instead take place on a GPU server).

In step 500A of FIG. 5A, a histology technician receives a block tissue sample and cuts the tissue sample into thin and thick slices. The thin slices are used to scan and the thick slices are used for microdissection once the relevant portion of a thin slice is identified. The technician may be located, for example, at a hospital, doctor's office, lab, or the like.

In step 500B, the technician stains the thin slice with, for example, Hematoxylin and Eosin (H&E) and scans the H&E glass slide to generate a digital tissue image, also called a Whole Slide Image (WSI). The scanning may use a 200,000×200,000 resolution scanner. A single WSI may be approximately 5 GB in size.

In step 500C, using client 401 or client 403, the technician uploads the WSI to web server 405 (there may be multiple web servers but only one is shown for simplicity). Web server 405 then transmits the WSI to file server 407, which stores a plurality of WSIs and related metadata. Web server 405 then uses a queueing engine running on the web server to determine which of GPU Servers 409 or 411 to use to break up the WSI into patches and extra features based on a load balancing algorithm. Once a GPU server is selected, the web server 405 transmits instructions to the selected GPU server (such as GPU server 409) to break up the WSI into patches and extract features using a convolutional neural network running on GPU server 409 (as discussed in more detail below with reference to step 505 of FIG. 5B).

In step 500D, once GPU server 409 (or 411) extracts the features using the convolutional neural network, it transmits a message to file server 407 to store metadata associated with WSI, the metadata including patch location, patch size (e.g., 400×400 pixels), and values of each of the features of the patch extracted by the GPU server 409. The metadata is then stored on file server 407 (associated with the stored WSI) and can be accessed by any GPU server (for example, 409 and 411) or web server 405.

In step 500E, once the metadata is generated and stored on file server 407 for all patches of the WSI, a notification is sent to a user such as a pathologist, by web server 405, that metadata for all patches of a WSI has been generated. The pathologist may be a user at, for example, client 403.

In step 500F, the user at client 403 selects one or more positive patches and zero or more negative patches, as discussed in more detail below with reference to step 507 of FIG. 5B. The user's selections are then transmitted from client 403 to web server 405, which in turn transmits them to file server 407 for storage as metadata associated with the WSI.

In step 500G, based on the user's selections and the extracted features, the web server generates a mask such as a microdissection mask as discussed in detail below with regard to steps 509, 511, and 513 of FIG. 5B.

In step 500H, the web server 405 transmits the mask to the technician at client 401. Then, in step 500J, the technician cuts the portion of the thick slide tissue sample identified in the mask by using laser 113.

Figure 5B:
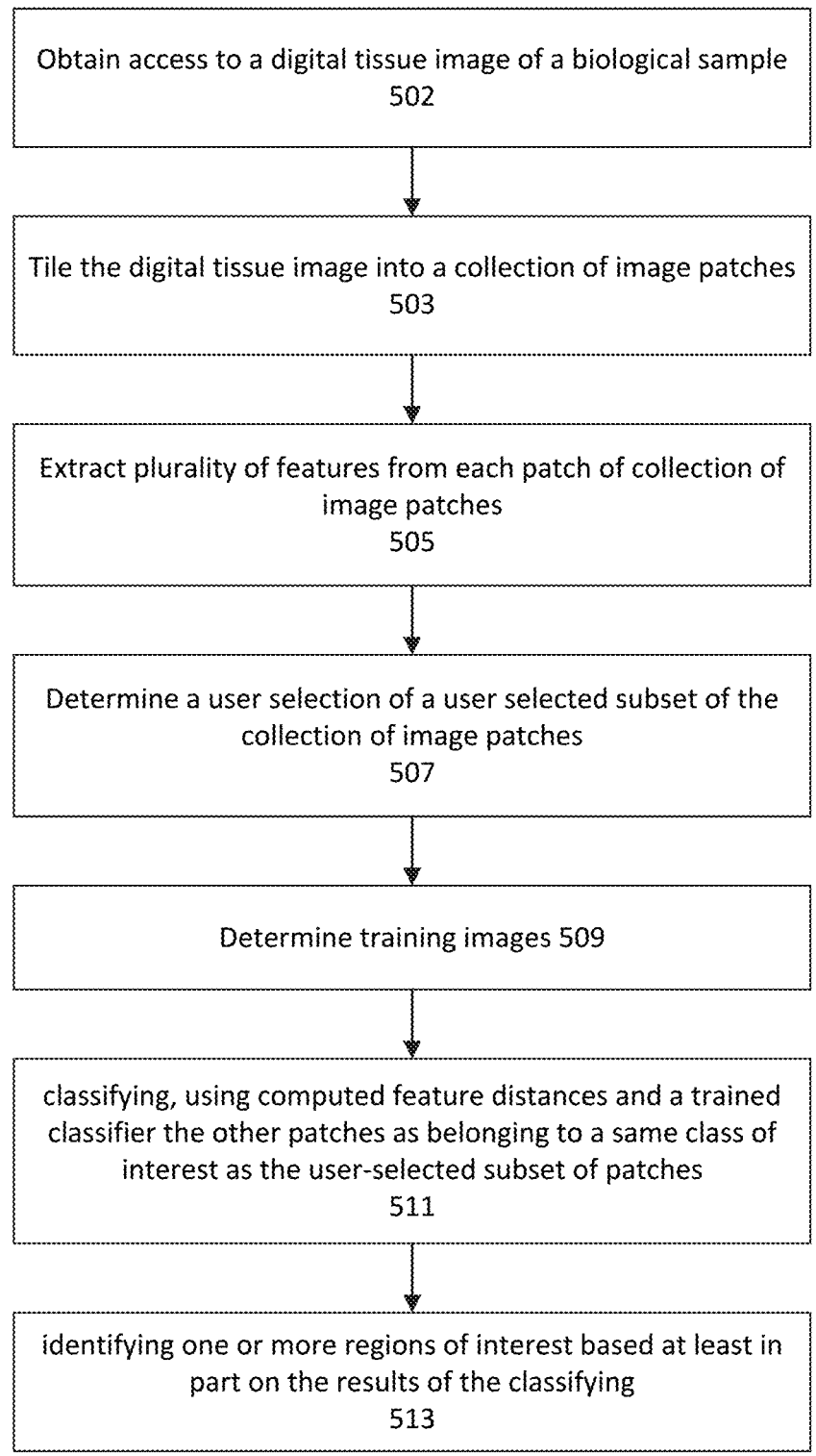

FIG. 5B illustrates a process carried out by an electronic device that can implement one or more aspects of an embodiment of the invention. More specifically, FIG. 5B shows a method for receiving a digital tissue image of a biological sample and determining the portions thereof likely to have cancer based, in part, on user input as well as machine learning. Once the portions are determined, as discussed with reference to FIG. 5A above, a portion of a biological sample may be microdissected for further processing. The steps of FIG. 5B may be performed in the order shown and may also be performed in another order. For example, step 503 may be performed after step 505 or step 507.

Prior to the CNN 319 receiving as an input the relevant tissue sample image (i.e., the test sample) (or patches of such an image) and providing as an output the image feature values, according to an embodiment of the present invention, the CNN 319 may be trained on generic images (i.e., not images of cancer cells and images without cancer cells). That is, CNN 319 may be considered a trained generic classifier. For example, the CNN 319 may be trained using ImageNet images. ImageNet is a large visual database for use in visual object recognition software research, which is organized according to the so-called WordNet hierarchy (which currently includes a large list of nouns), in which each node of the hierarchy includes a large number of images (e.g., 500). See, e.g., http://www.image-net.org/. For example, ImageNet includes a large number of images for each of the following nouns, organized in a hierarchy: animal, vertebrae, mammal, placental, primate, monkey, baboon, mandrill. Each category may include synonyms and/or related terms such as animal, which includes related terms animate being, beast, and creature. The large number of images for each term in WordNet (i.e., each class of images) show the relevant subject in various poses, times, ages, locations, image qualities, colors, with additional objects, backgrounds, and the like. There may be, for example, 1000 nodes in the hierarchy. The plurality of images used to originally train CNN 319 may, for example, include a plurality of images (or patches) of various generic images not necessarily related to any diseases. In one example, CNN 319 has been previously trained on hundreds of thousands or even millions of such images.

CNN 319, positive one-class SVM 311, negative one-class SVM 313, two-class SVM 315, one-class SVM training patches 302F, two-class SVM training patches 302J, test patches 323, and regions of interest 321 may also be stored and executed on servers 107-109 or may instead be stored and executed on one or more client devices 102-106 or a combination of servers 107-109 and/or client devices 102-106. More specifically, SVMs 311, 313 and 315 may be stored and executed on web server 405 of FIG. 4C.

Trained CNN 319 may be used to extract features from patches of images of biological samples for which the classification is unknown (i.e., test patches). Once the CNN 319 is trained, it is ready for use with "test" patches. Test patches, such as test patches 323, are patches from an actual patient's tissue sample that may have been captured using the microscope, ocular assembly, camera, and slide platform of optical microscope system 111.

Figure 11A:
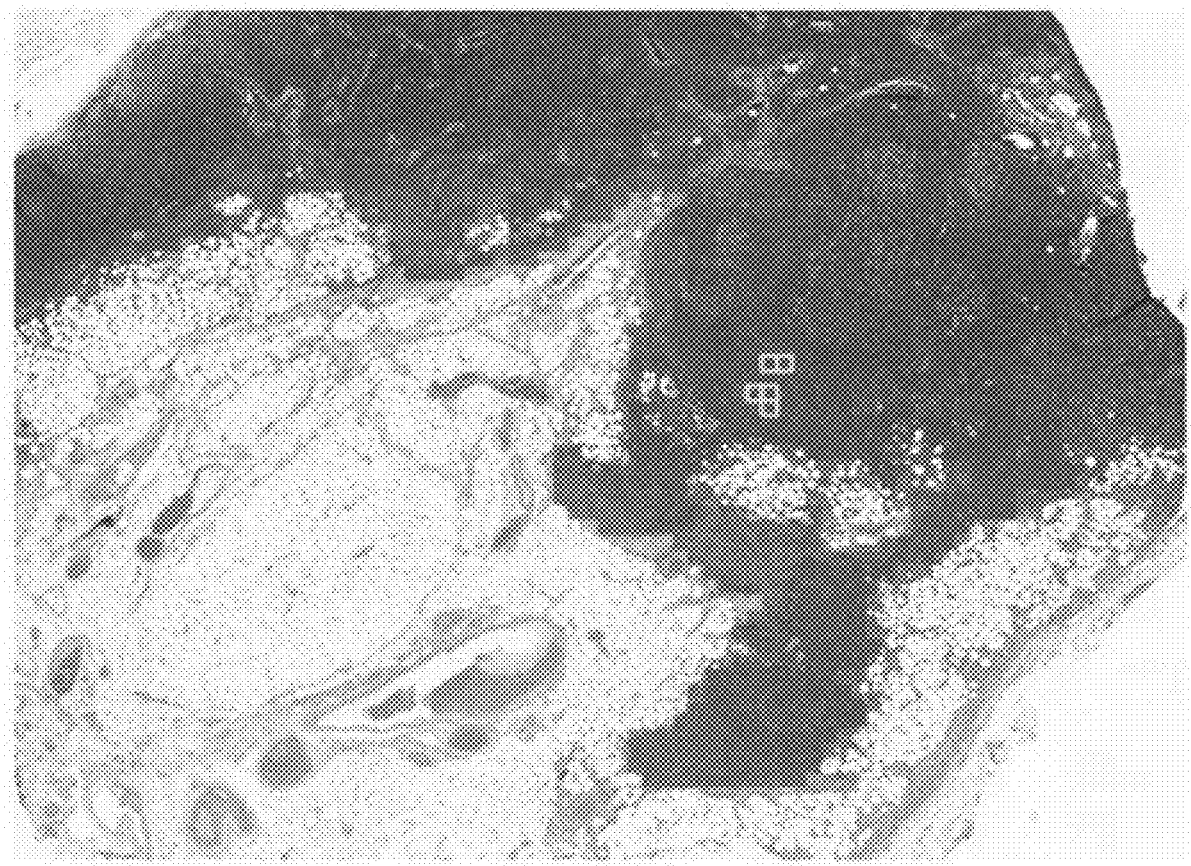
Figure 11B:
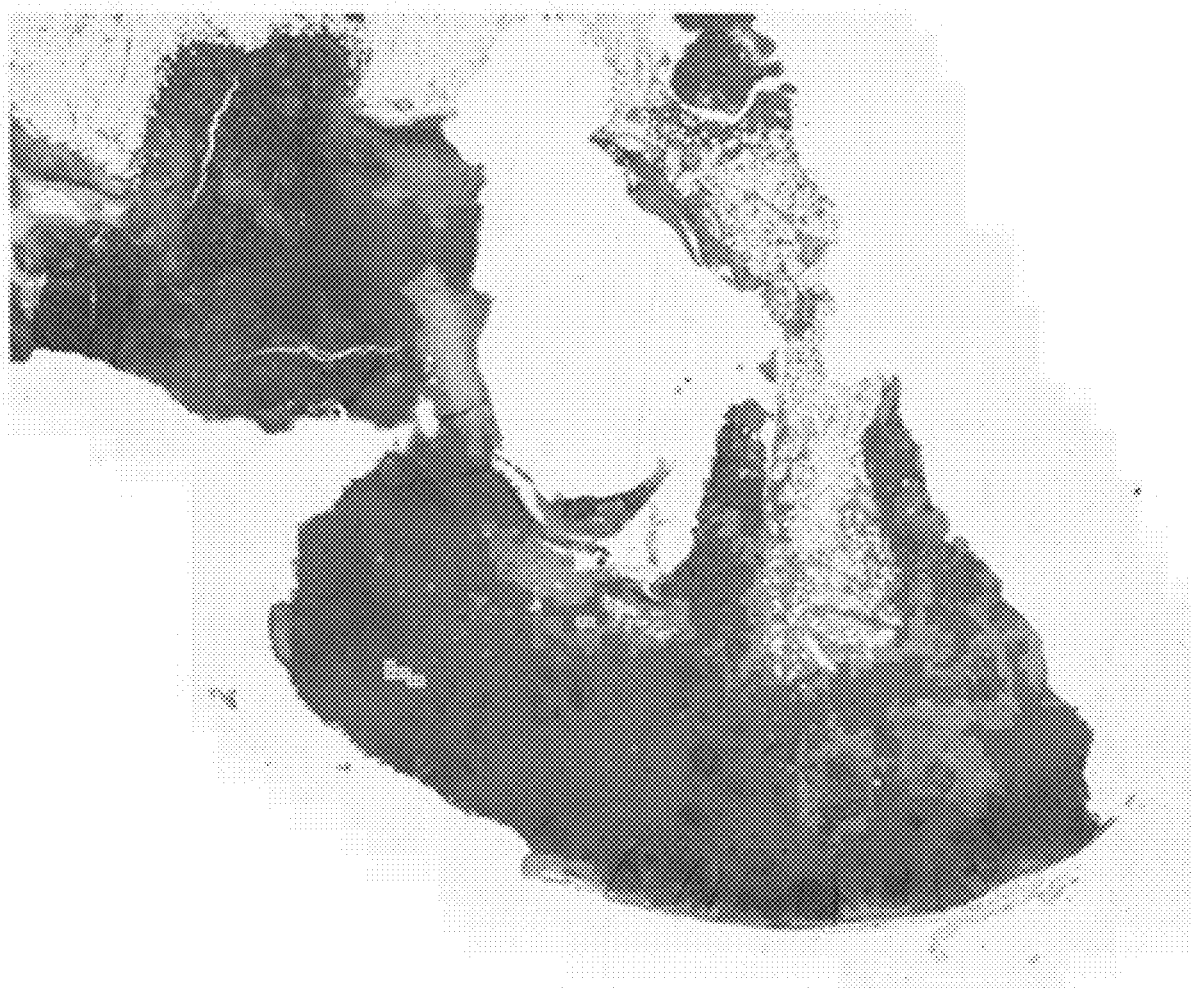

In step 502, the image processing engine 301 obtains access to a digital tissue image of a biological sample. The user may be provided instructions regarding selecting a digital tissue image of a biological sample (i.e., a whole slide image), as shown on FIG. 11C. The digital image may in various forms, for example, SVS, TIFF, VMS, VMU, NDPI, SCN, MRXS, SVSLIDE, BIF, PDF, JPG, BMP, GIF and any other digital image format. Moreover, the digital image may be located on a server, it may be a large image (many GB in size), the image may be stored in the cloud and all analysis in FIG. 5B may be performed in the cloud. The cloud may include servers 107-109. However, the steps of FIG. 5B may also be performed at one or more client devices 102-106 or a combination of servers 107-109 and/or client devices 102-106. The processing may be parallel and take place on multiple servers. The digital image may include biological sample metadata including digital information associated with at least one of the following: a tissue type, a tissue donor, a scanner, a stain, a staining technique, an identifier of a preparer, an image size, a sample identifier, a tracking identifier, a version number, a file type, an image date, a symptom, a diagnosis, an identifying information of treating physician, a medical history of the tissue donor, a demographic information of the tissue donor, a medical history of family of the tissue donor, and a species of the tissue donor.

In step 503, tile generation engine 303 tiles the digital tissue image into a collection of image patches 323 (test patches 323). Each tile/patch in the test patches 323 may be, for example, less than or equal to 1000×1000 pixels, less than or equal to 400×400 pixels, less than or equal to 256×256 pixels or any other suitable number of pixels. The tiling step may be performed iteratively or in parallel by one or more computers. Tiling may include creating image patches that are of a uniform size and a uniform shape. The size of the patch may be a function of the size of previous positive patches 302D and previous negative patches 302E, patches previously selected by pathologists as being positive or negative for cancer, grade of cancer, the particular type or grade of suspected cancer of test patches 323, or some other disease. For example, if patches previously selected by pathologists as being positive or negative were 400×400 patches, the tile generation engine 303 may tile the image into same size (400×400) patches or, within 1%, 3%, 5%, 10%, 20%, 25%, or 30% of the size of the previous patches.

In step 503, the test patches 323 may or may not be of a uniform size and shape. For example, one patch may be 400×400 and another patch may be 300×300 or 300×200. The patches also need not be squares, they may be rectangles, circles, ovals or more complex shapes. Various processes may be used for tiling such as Penrose tiling, bulk exclusion, and/or bound boxes.

In step 503, the generated patches may be overlapping or non-overlapping. That is, the same area of the digital image may or may not be included in more than one tile/patch.

The generated patches are stored as test patches 323 in a memory of servers 107-109 and/or client devices 102-106 or a combination of servers 107-109 and/or client devices 102-106.

In step 505, the feature extraction engine 305 extracts a plurality of features from each patch of test patches 323 and stores them in test patches 323 as metadata or a separate data structure or, outside of test patches 323 in a separate database/data structure. In particular, the feature extraction engine 305 extracts image features from patches 323. In one embodiment, features extraction engine 305 extracts features identified as useful byCNN 319, for example, one based on Inception v3 and trained on a variety of diverse images such as, for example, the ImageNet images. The feature extraction engine 305 makes use of the fully trained CNN 319 to extract features from images. In one embodiment, feature extraction engine 305 communicates with trained CNN 319 and provides it, either one at a time or in a single call/message, the patches 323 for feature extraction. As CNN 319 receives each patch from feature extraction engine 305, processes each of the patches 323 through the layers shown in FIG. 4B beginning with the top-most convolutional layer to the second from the bottom linear layer. The linear layer provides, as output, a number of features (e.g., 2048) representing the input patch and provides the 2048 feature values to feature extraction engine 305, as shown in FIG. 3. These values may be provided to feature extraction engine 305 by CNN 319 in, for example, an array, vector, linked list, or other suitable data structure. The features may then be stored in test patches 323.

In step 505, the feature extraction engine 305 may identify/select patches from test patches 323 as a function of pixel content, instead of extracting features from all test patches 323. For example, identification may include filtering the patches based on color channels of the pixels within the image patches. For example, the identification may be made as a function of the variance of the patches. The variance of the patches may be based on the variance of the Red Green Blue (RGB) channels and/or Hue, Saturation, Value (HSV) and/or Hue Saturation and/or Luminosity (HLS) and/or Hue Saturation Intensity (HIS) in a particular patch. This step helps insure that only patches that include cells are considered. Once step 505 is complete, only patches with cells may be identified/selected for feature extraction.

Figure 7A:
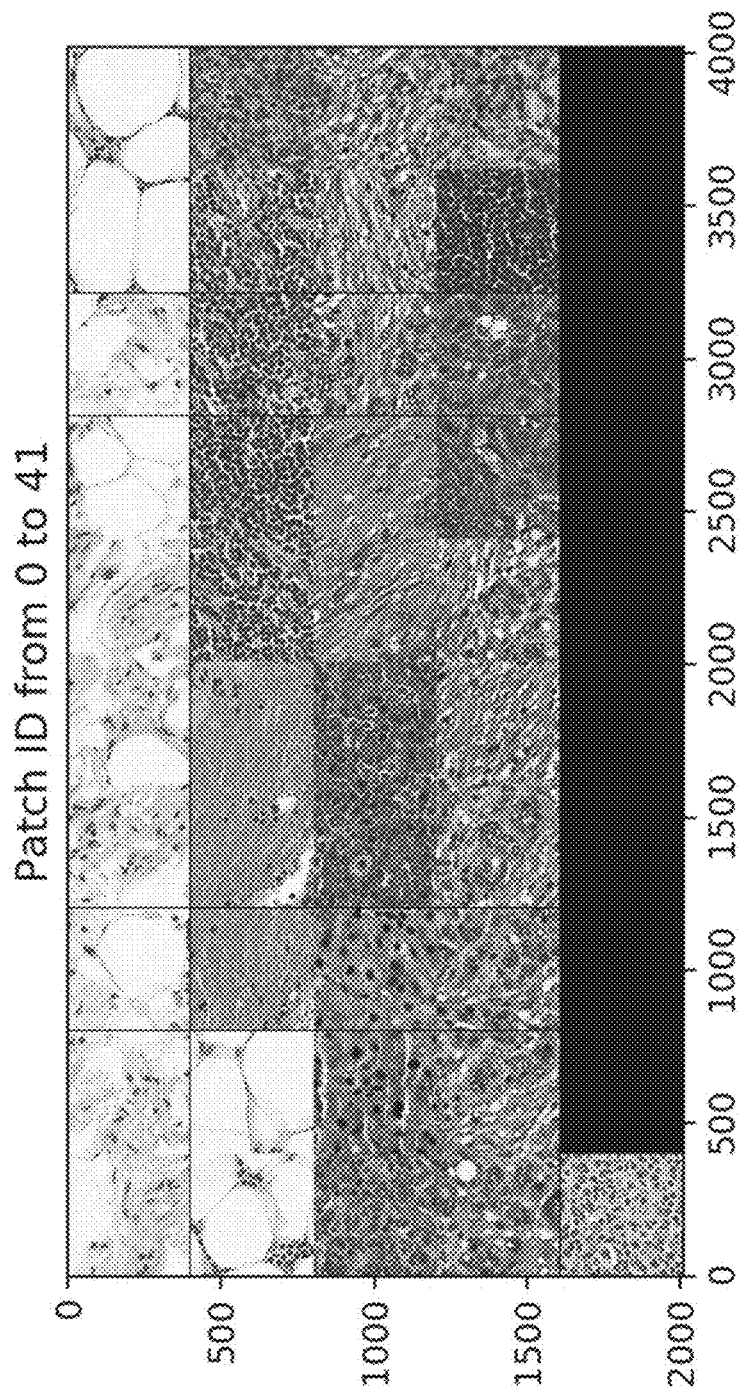
FIGS. 7A-7C illustrate diagrams showing a plurality of patches of tissue to be processed by an electronic device that implements one or more aspects of an embodiment of the invention.
Figure 7B:
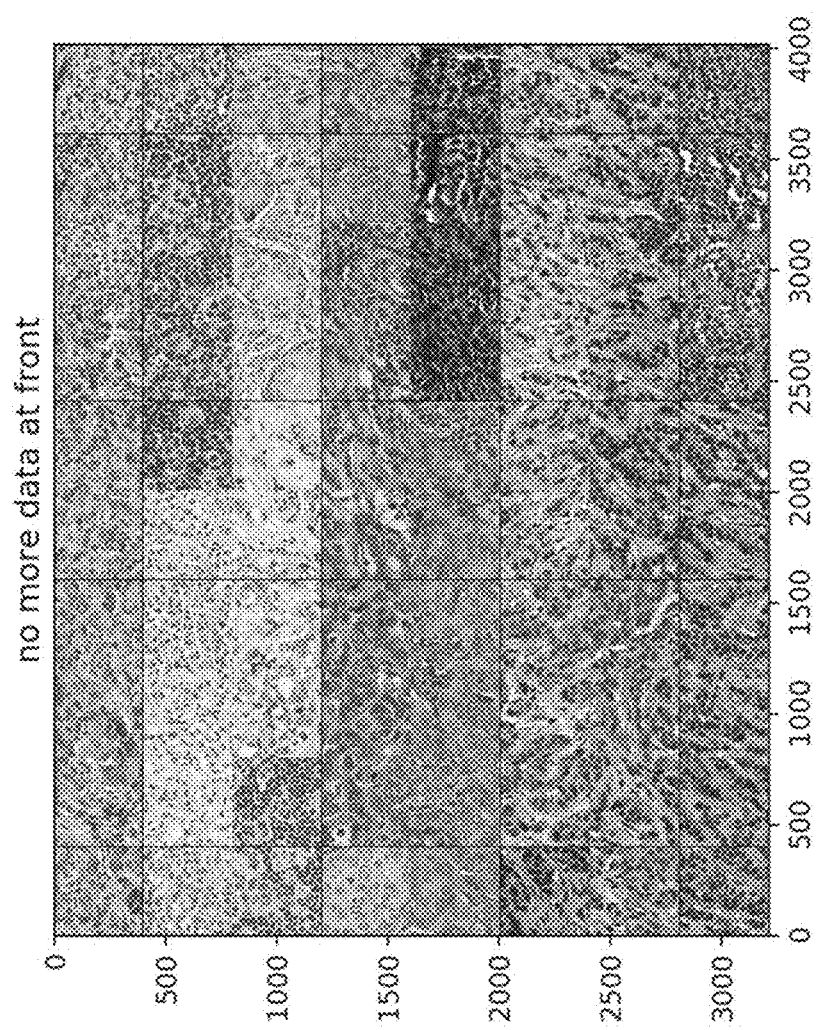
Figure 7C:
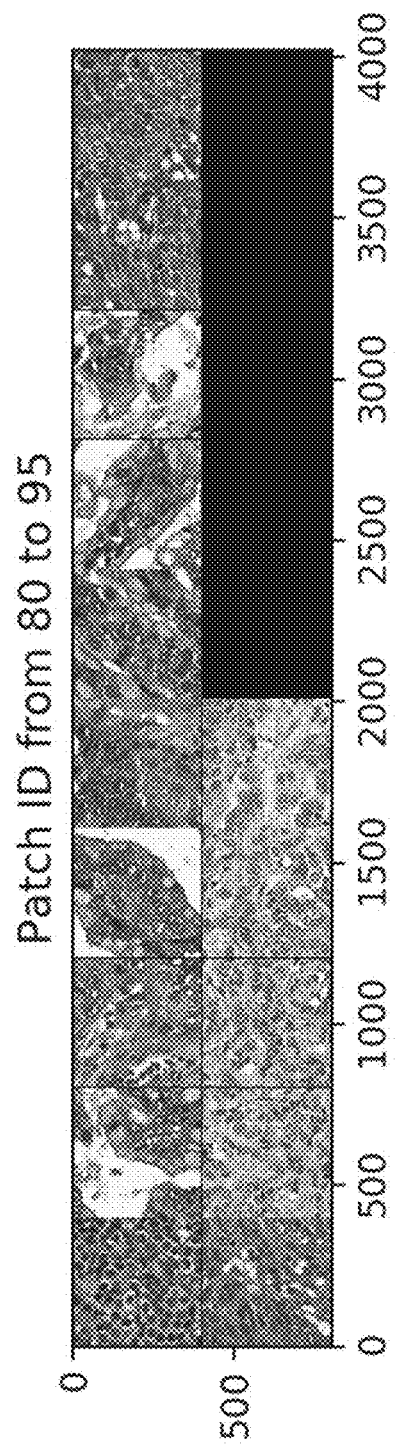
Figure 11D:
Figure 11D:
Figure 11D:
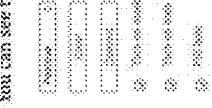
Figure 11D:
Figure 11E:
Figure 11F:
Figure 11G:
Figure 11H:

In step 507, the user selection engine 307 determines a user selection of a user selected subset of the collection of image patches. As illustrated in FIG. 11D, a user may be provided with instructions regarding making the user selection. That is, a Graphical User Interface (GUI) controlled by the user selection engine 307 shows a user (such as a pathologist or one or more pathologists at one or more sites) the test patches 323. For example, FIGS. 7A-7C show a plurality of patches that may be shown to a user. A user may be shown a GUI by user selection engine 307 similar to FIG. 7A, 7B, or 7C (more or less patches may be shown) on an I/O Interface 240 such a screen, smartphone screen, tablet, touchscreen, or the like. FIGS. 11E and 11F show a GUI in a state after a user has selected one positive patch. A user may select the positive/negative dropdown to indicate whether he or she is selecting positive or negative patches. Once the user selects positive or negative, he or she may click on one or more patches to select them. If the user believes he or she may have made an error in the selection, he or she may click the clear button and begin selecting patches anew. If the "fill hole" checkbox is checked as shown in FIG. 11E, then, when there is a hole (an area of one or more patches not selected by the user) within an area selected by the user as being positive for cancer, the hole (unselected area) will nevertheless be treated as if it was selected by the user as being positive for cancer and accordingly filled in (the same would be true if the user was selecting negative patches). Once a user is sure he or she has selected all of the positive or negative patches he or she desires, he or she may click the commit button.

First, the user may select whether to select positive patches (i.e., patches the user believes to be positive for cancer, a particular type or grade of cancer, or other relevant disease) or negative patches (i.e., patches the user believes to be negative for cancer, a particular type or grade of cancer, or other relevant disease). Once that selection has been made, the user will select one or more positive or negative patches (depending on whether the user selected negative or positive patches above). Optionally, the user may select positive patches first or may only select positive patches and not negative patches. Once the user is satisfied that he or she has selected an adequate number of patches, he may select the "commit" (or similar) button to let user selection engine 307 know that he or she finished selecting a particular set (positive or negative) of patches.

Any positive patches selected by the user are then stored in SVM training patches 302F and, in particular, current positive patches 302B and any negative patches selected by the user are stored in current negative patches 302C. The entire selected patch may be stored or an identifier of the patch in test patches 323 may be referenced (for example, if there are 10,000 test patches 323 and each has an identifier between 1 and 10,000, current positive patches 302B and current negative patches 302C may store a plurality of identifiers that each reference a test patch in test patches 323. For example, following the user selection in step 507, user selection engine 307 may store a linked list in current positive patches 302B with identifiers 8, 500, 1011, 5000 and 9899. Similarly, the user selection engine 307 may store a linked list in current negative patches 302C with identifiers 10, 550, 1015, 4020 and 9299.

The user's selection helps image processing engine 301 correctly determine other test patches 323 that are either likely negative or likely positive for cancer. Assuming the user correctly selects positive and negative patches, the image processing engine 301 may then compare patches it knows to be positive (via user selection of the positive patches in step 507) with other patches in test patches 323 and select such patches as likely positive based on feature distances between a candidate test patch in test patches 323 and the user selected positive patches, as discussed in more detail below with respect to positive one-class Support Vector Machine (SVM) 311, negative one-class SVM 313, and two-class SVM 315. The image processing engine may similarly compare user selected negative patches and test patches 323 to determine likely negative patches.

Although it is possible for image processing engine 301 to select likely positive or likely negative patches using CNN 319 trained with generic images in step 501 and without SVMs 311, 313 and 315, as discussed in detail below, such a process, as shown in FIGS. 6A-6D, may have classification errors, as discussed in more detail below.

Figure 6A:
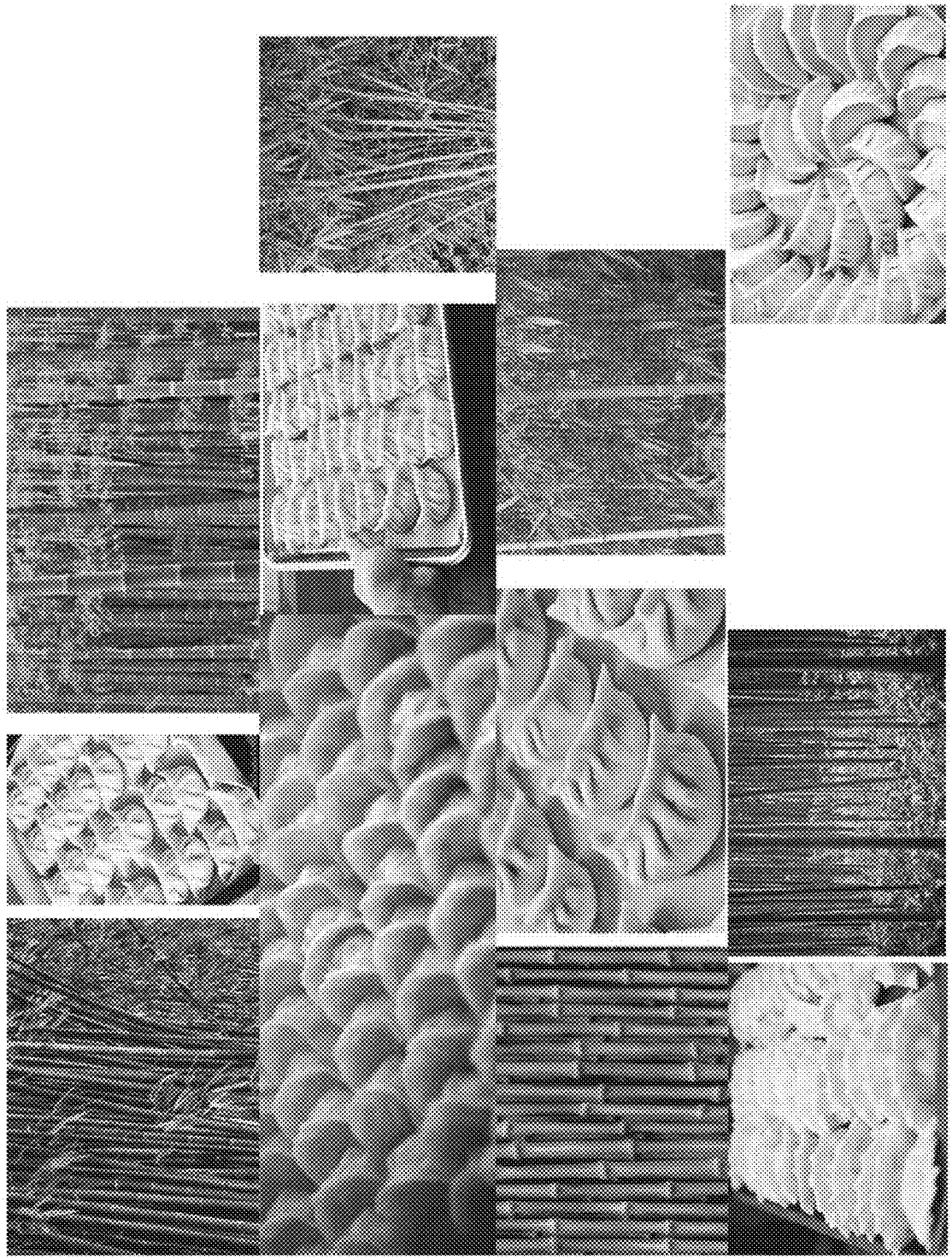
FIG. 6A illustrates two classes of objects, according to one or more aspects of an embodiment of the invention.

FIG. 6A shows two classes of images: (1) pines and bamboo ("bamboo"); and (2) dumplings. The images in FIG. 6A are input into a CNN, for example, Inception v3, which has been trained on generic images such as ImageNet. Based on the ImageNet training, the linear layer of the CNN will generate 2048 features for each of the test images shown in FIG. 6A. Image processing engine 301 will then calculate the distance (such as the Euclidian/L2 distance of the 2048 features extracted by the linear layer of the CNN) between each image and each other image (i.e., distance between image pairs). An analysis may be performed to determine which of the 2048 features are particularly important and increase their weight to generate a modified L2 distance weighing certain features more heavily than others. Using a priori distance thresholds, the system would then classify pairs of images as being in the same class. Once a user makes a selection as to a positive image/patch, the system would then find matching patches using the above analysis. The same analysis can be performed for a negative patch selected by a user.

Figure 6B:
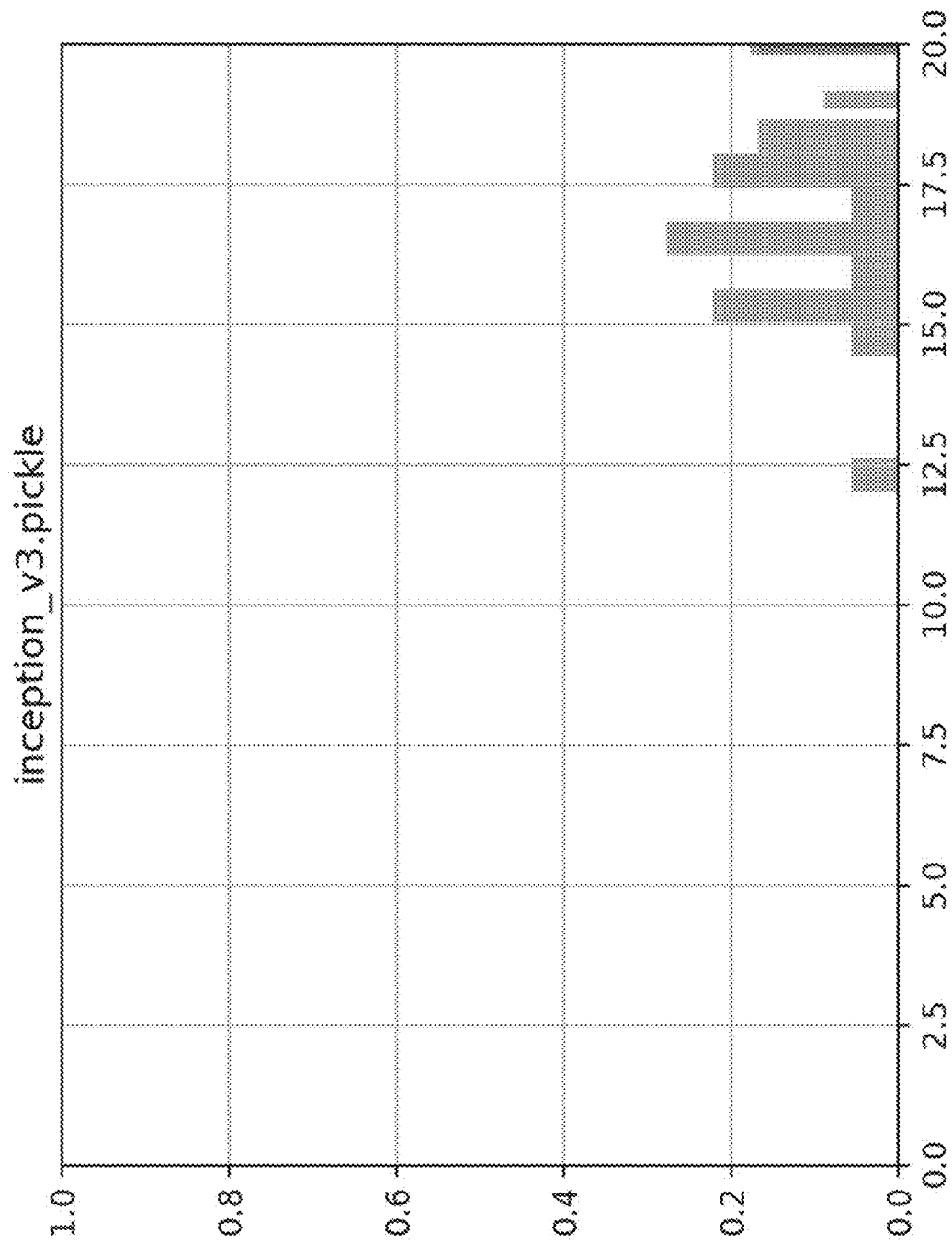
FIG. 6B illustrates a neural network's classification results of the objects in FIG. 6A.

FIG. 6B illustrates a vertical bar graph showing the results of the classification of the images in FIG. 6A, as discussed above. The x-axis represents the difference in L2 distances of pairs (of values of the 2048 features extracted by the CNN 319). The y-axis is a normalized histogram showing the normalized number of values of pairs that fall into that L2 distance.

According to FIG. 6B, each green bar (i.e., the first 8 bars from the left) shows a matched pair (i.e., bamboo-bamboo or dumpling-dumpling), whereas each red bar (the final 2 bars near the right end) shows an unmatched pair (i.e., bamboo-dumpling). As suggested by FIG. 6B, it may be possible for a user to a priori determine the L2 distance threshold to programmatically separate matched pairs from unmatched pairs based on their L2 distance. For example, if an L2 distance of approximately 18 was chosen (where any pair of images for which the L2 distance was less than or equal to 18 was considered matched and any pair of images for which the L2 distance was more than 18 was considered unmatched), this may appear to provide accurate results of matched pairs and unmatched pairs.

Figure 6C:
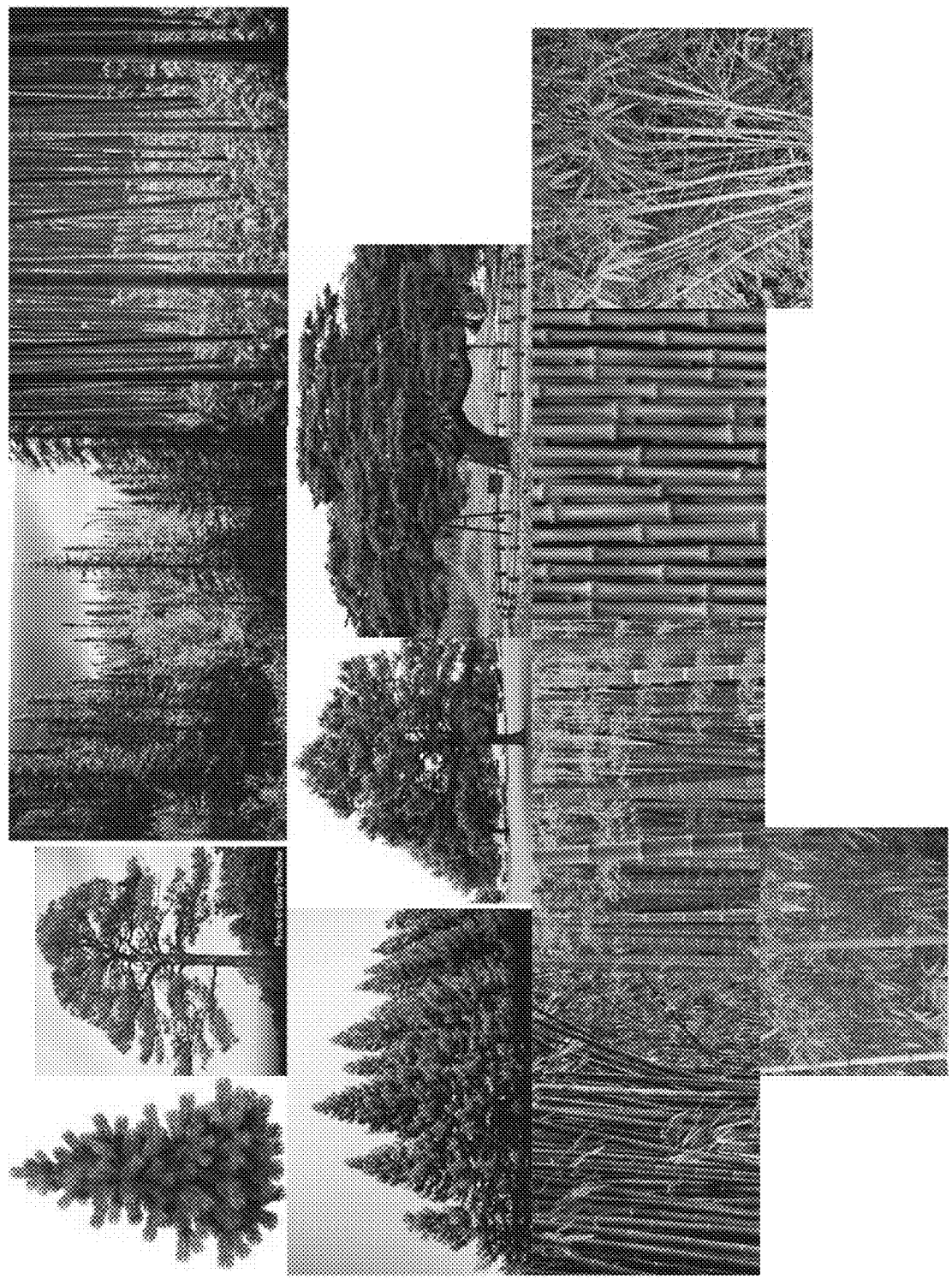
FIG. 6C illustrates two classes of objects, according to one or more aspects of an embodiment of the invention.
Figure 6D:
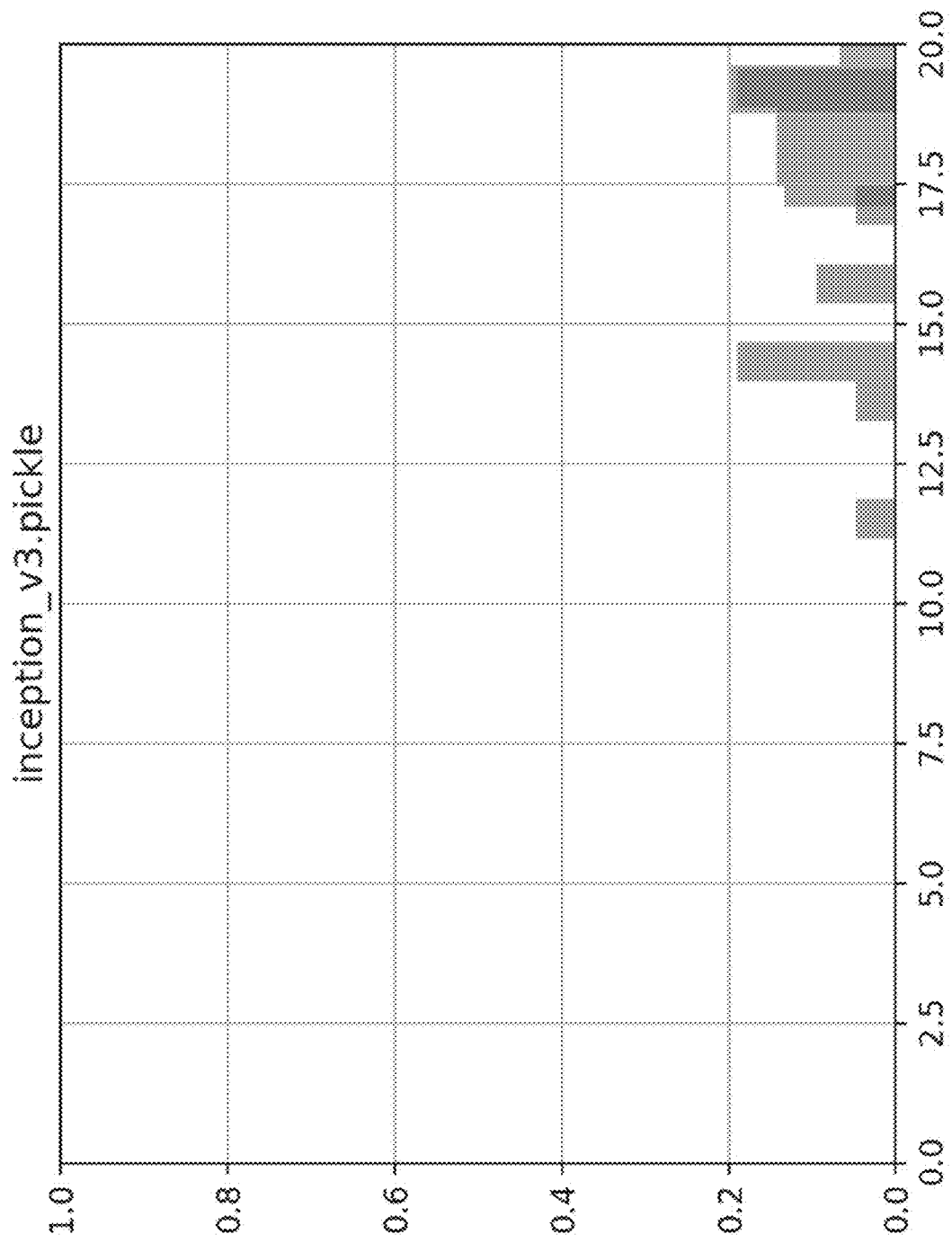
FIG. 6D illustrates a neural network's classification results of the objects in FIG. 6C.

However, as can be seen in FIGS. 6C-6D, the above approach may not work well for other sets of images. FIG. 6C, similarly to FIG. 6A, shows two classes of images: (1) bamboo; and (2) dumplings. Similarly to FIG. 6B, FIG. 6D illustrates a vertical bar graph showing the results of the classification of the images in FIG. 6C. As can be seen in FIG. 6D, however, using the same process as in FIGS. 6A-6B, several mismatched pairs (red bars) have lower L2 distances than matched pairs (green bars). Thus, it may not be possible to a priori select an L2 distance threshold that would include only matched pairs with an L2 distance below or equal to the threshold and only unmatched pairs with an L2 distance above the threshold.

And in pathology samples, the variation in test images/patches (of, for example, color and intensity) makes classification even more difficult than in FIGS. 6A-6D. Thus, using the matching method of FIGS. 6A-6D with pathology samples may lead to even more incorrectly matched pairs of images/patches.

Figure 5C:
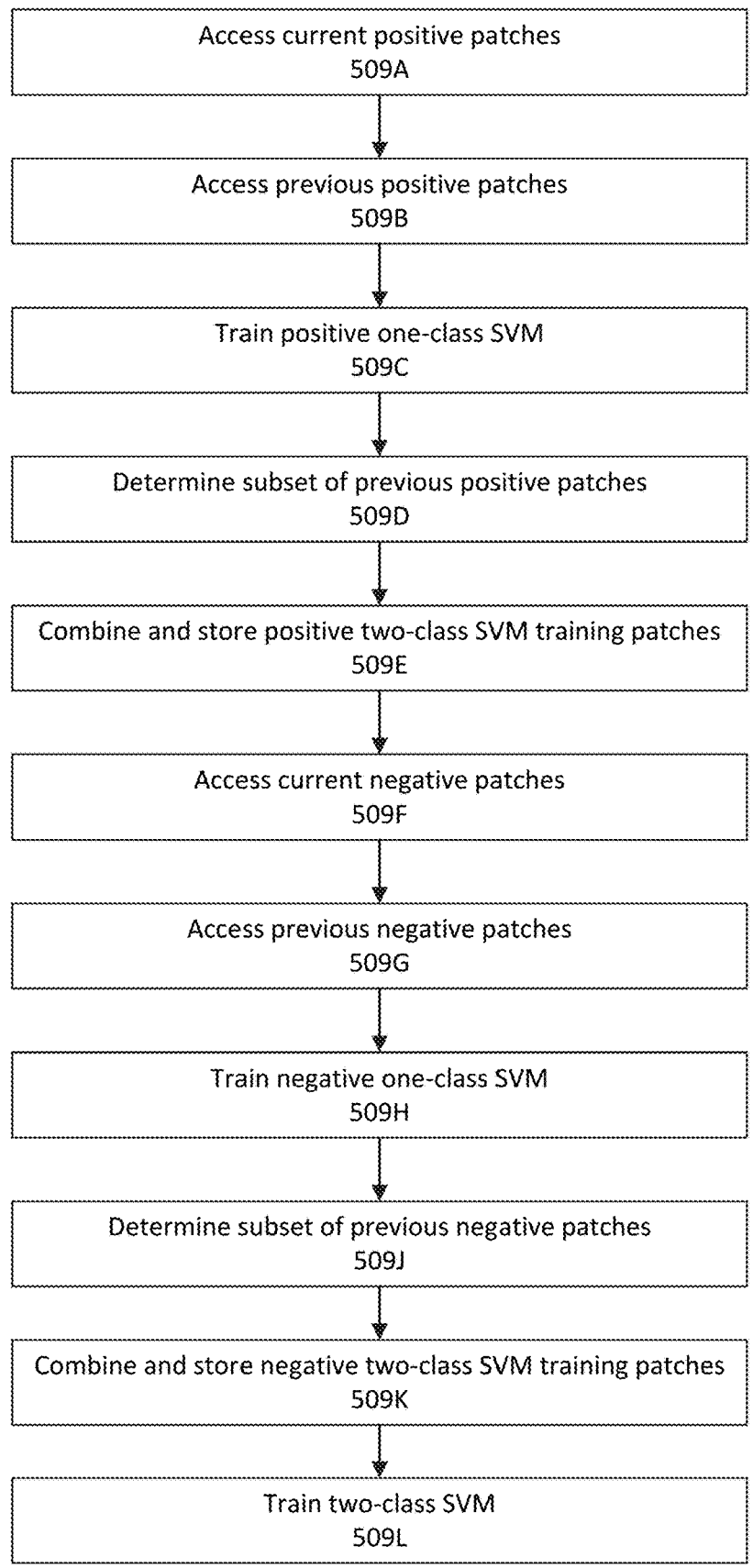

Referring back to FIG. 5B, once a user selection of positive and/or negative patches is determined in step 507, the two-class SVM 315 training images are determined in step 509. Step 509 is described in further detail with reference to in FIG. 5C below.

In step 509A, the SVM training engine 308 accesses the current positive patches 302B (i.e., the positive patches selected by the user from the current test patches 323) (in general, data such as current positive patches 302B may be accessed directly or may be provided by the previous or other engine, in this case, user selection engine 307 to the current engine, SVM training engine 308). In step 509B, SVM training engine 308 then accesses the previous positive patches 302D. For example, SVM training engine 308 may select all or a predetermined number (such as 2, 3, 5, 10, 15, 20, 30, 50, or 100) of the most recently selected previous positive patches 302D or it may select all or a predetermined number of previous positive patches 302D that were selected from previous test patches involving the same type of cancer/disease as suspected in test patches 323 or it may select all or a predetermined number of previous positive patches 302D that were selected by the current user.

There is a high level of probability that the current positive patches 302B are accurate since a user selected them. However, previous positive patches 302D include patches from other images/patches (not current test patches 323). Thus, it is necessary to determine whether they are relevant to test patches 323 by only selecting relevant previous positive patches 302D as compared to current positive patches 302B. Such determination takes place in step 509C-509D.

Figure 8:
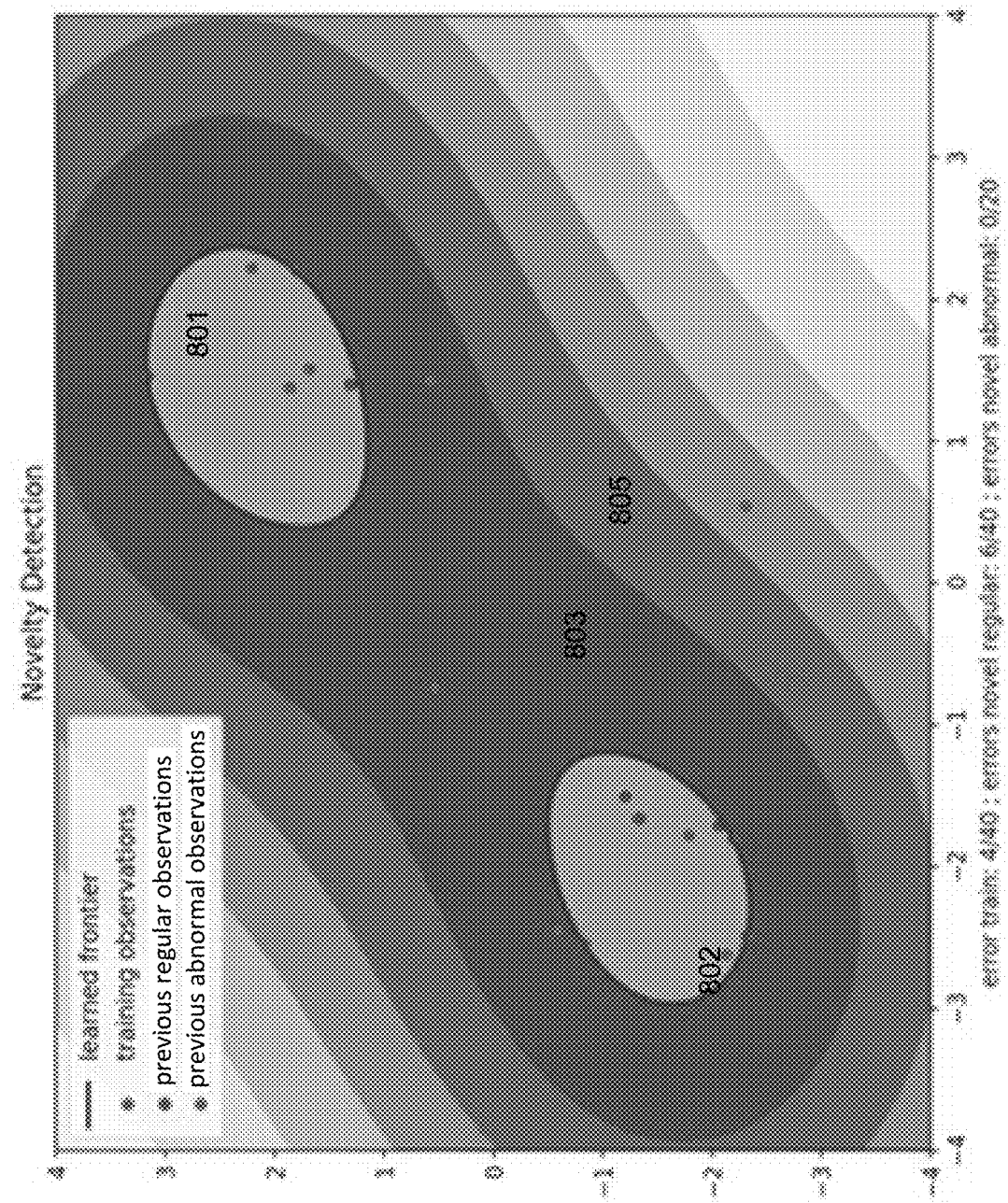
FIG. 8 illustrates one-class Support Vector Machine (SVM) with Radial Basis Function (RBF) kernel, according to one or more aspects of an embodiment of the invention.

In step 509C, the SVM training engine 308 accesses and trains the positive one-class SVM 311 as shown in FIG. 8. An SVM is a supervised learning model with associated learning algorithms that analyzes data used for classification and regression analysis (in our case, classification). An SVM first receives as input training data (e.g. images) of one or more classes. It then builds a model based on the training data that is able to determine the class in which a new test image belongs. A one-class SVM has a single class of images that it classifies.

FIG. 8 illustrates one example of the results of using a one-class SVM with Radial Basis Function (RBF) kernel, according to one or more aspects of an embodiment of the present invention. As can be seen, FIG. 8 shows multiple bands including 801, 803, and 805. FIG. 8 also shows green training observations 802, which are the patches used to train the positive one-class SVM 311. The training observations include only the current positive patches 302B (or a predetermined number of current positive patches 302B).

Once the current positive patches 302B are input into the positive one-class SVM 311 to train the positive one-class SVM 311, the SVM generates bands using a Gaussian distribution based on the data points (vectors) in the 2048-dimension feature space used in a present embodiment to describe the current positive patches 302B. Then, once test patches are input into the positive one-class SVM 311, the test patches 323 within the two innermost pink ellipse-like regions 801 are most similar to the current positive patches 302B. The innermost, darkest blue band 803 that fully encloses the two pink regions 801, would include patches that are less similar than the patches in the innermost pink regions (or, generally, the training patches (current positive patches 302B)). Region 805 is even further from the pink regions 801 and patches in those regions would be even less similar than patches in pink regions 801.

SVM training engine 308 determines which bands signify inclusion in the class of the training data (in this case, positive patches) and which bands signify exclusion. For example, SVM training engine 308 may determine (or it may be predetermined) that only previous positive patches 302D (observations) determined to be in regions 801 and 803 signify inclusion in the same class as the training data (in this example, current positive patches 302B). That is, previous positive patches 302D that positive one-class SVM 311 determines are either in regions 801 or 803 would be considered to be in the same class as current positive patches 302B. That is, following training, SVM training engine 308 would provide as an input to positive one-class SVM 311 a subset (or all of) of previous positive patches 302D. The positive one-class SVM 311 would determine the region of each patch based on the training data and only determine the previous positive patches 302D that are in regions 801 or 803 to be in the same class.

It is noted that the above process of determining which of the previous positive patches 302D are in the same class as current positive patches 302B via the positive one-class SVM 311 in step 509C may be performed by other means of outlier detection. For example, elliptic envelope, or isolation forest (which, for example, detects data-anomalies using binary trees) may be used in place of, or in combination with, a one-class SVM to determine which patches in previous positive patches 302D to remove as outliers.

Once SVM training engine 308 determines which previous positive patches 302D are in the same class as current positive patches 302B, in step 509E, both current positive patches 302B and the selected previous positive patches 302D (selected by the positive one-class SVM) are combined and stored as two-class positive training patches 302G (the patches may be stored as images or as identifiers to the relevant test patches 323). These patches 302G are then, in turn, used to train two-class SVM 315.

A similar process may then take place for negative patches. That is, in step 509F, current negative patches 302C may be accessed, similar to step 509A. In step 509G, previous negative patches 302E may be accessed, similar to step 509B. In step 509H, negative one-class SVM 313 may be trained, similar to step 509C. In step 509J, a subset of previous negative patches 302E may be determined, similar to step 509D. In step 509K, the current negative patches 302C may be combined with the subset of previous negative patches 302E and stored in two-class negative training patches 302H, similar to step 509E.

As an alternative, instead of using negative one-class SVM 313 to perform steps 509F-509K, the positive one-class SVM 311 may be used for both positive and negative patches. That is, for example, if no current negative patches 302C have been provided by the user, the SVM training engine 308 may use positive one-class SVM 311 to determine the previous negative patches to use as two-class negative training patches 302H.

In particular, there would be no current negative patches to access in step 509F so that step would be skipped. In step 509G, previous negative patches 302E would be accessed. Step 509H could be skipped and, instead, the trained positive one-class SVM would be used. Step 509J would be modified, instead of selecting previous negative patches 302E that are within inner bands 801 and 803, only previous negative patches 302E that are not within bands 801 and 803 would be selected. That is, only previous negative patches 302E that are not sufficiently similar to current positive patches 302B would be selected (bands 805, etc.). The selected previous negative patches 302E (or identifiers thereof) would then be stored in two-class negative training patches 302H. If there are no previous negative patches 302E, SVM training engine 308 may store stock negative patches selected by users of other systems or never selected by any user but that have characteristics of negative patches. In the alternative, these stock negative patches may be stored in previous negative patches 302E.

Once the two-class positive training patches 302G and two-class negative training patches 302H have been determined, the SVM training engine 308 proceeds to train two-class SVM 315 with patches 302G and 302H in step 509L. That is, the two classes of two-class SVM 315 are positive patches and negative patches and will be stored by the respective positive and negative patches determined by one-class SVMs 311 and 313.

Figure 9A:
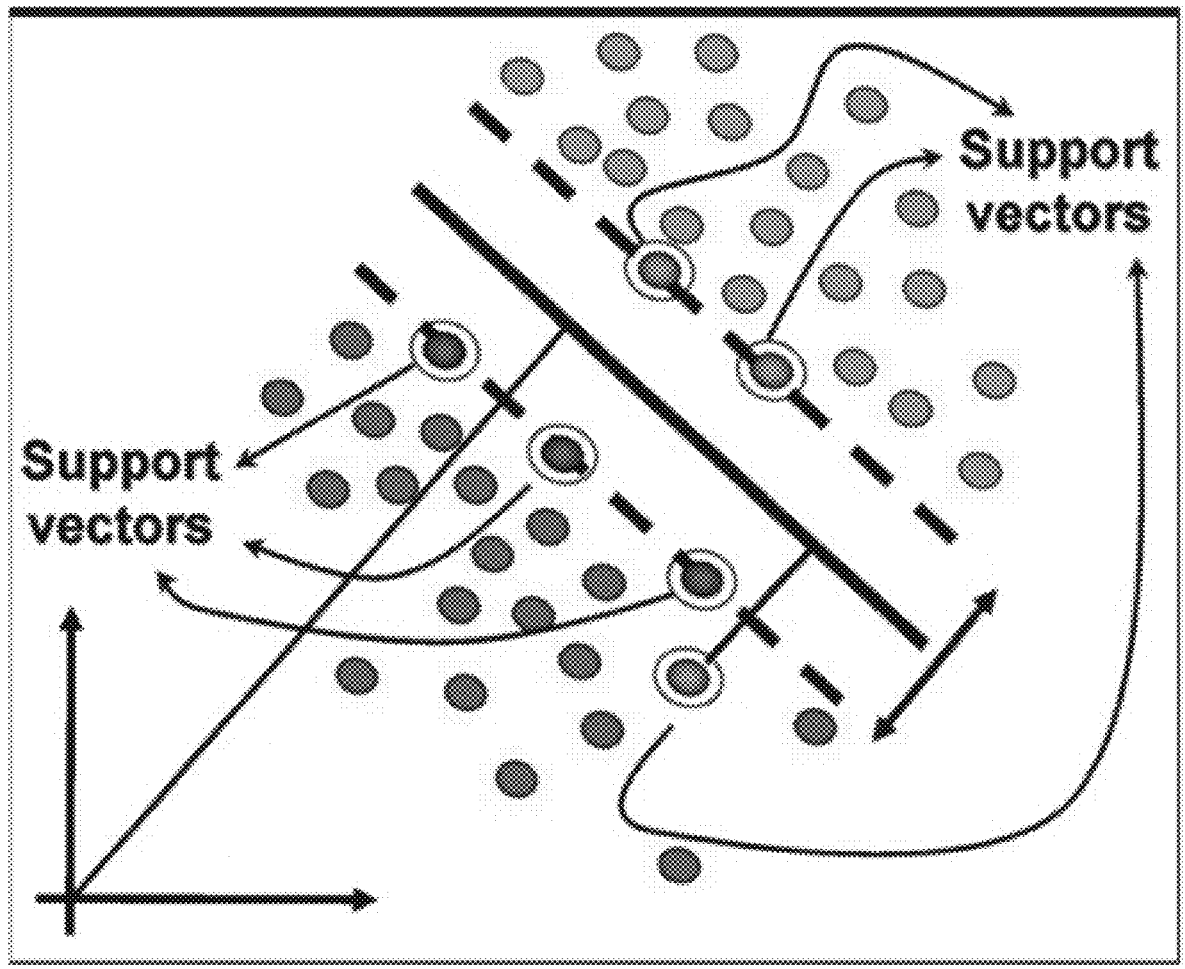
FIGS. 9A-9B illustrates a two-class SVM, according to one or more aspects of an embodiment of the invention.
Figure 9B:
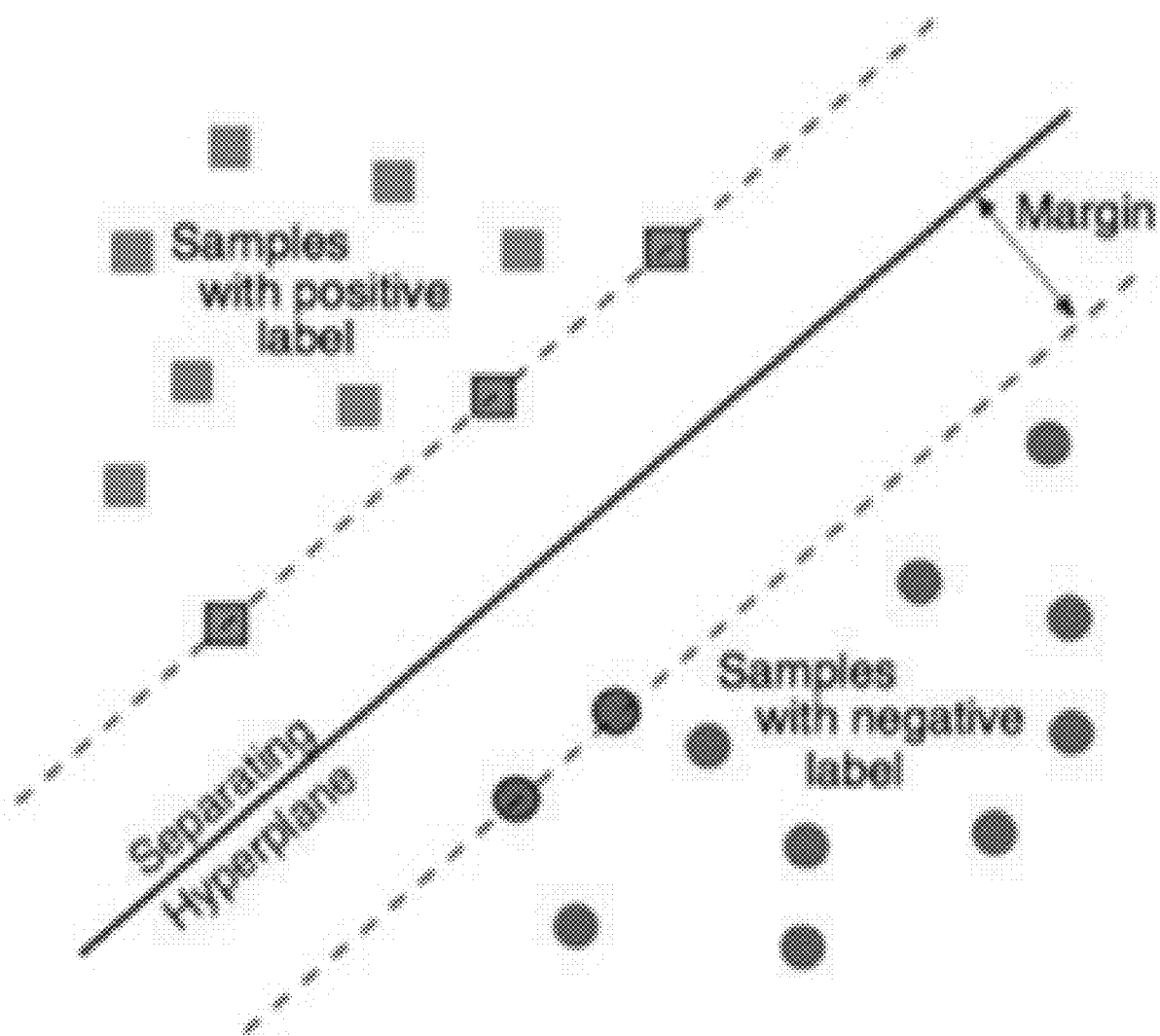

In step 509L, once two-class positive training patches 302G (shown with one exception on the top right of FIG. 9A) and two-class negative training patches 302H (shown on the bottom left of FIG. 9A) have been provided to the (linear) two-class SVM 315, the two-class SVM 315 selects negative support vectors (encircled patches the bottom dashed line crosses) and positive support vectors (encircled patches the top dashed line crosses) so as to maximize the margin width (the width between the two parallel dashed lines). The hyperplane is the solid line shown at the midpoint between the two dashed lines. FIG. 9B is similar.

Once the hyperplane is determined in two-class SVM 315 in step 509L, step 509 of FIG. 5B is complete.

In step 511, the classification engine 309 provides as an input all or a subset of the test patches 323 to now trained two-class SVM 315. The trained two-class SVM 315 then classifies each of test patches 323 as either being a positive patch (positive for cancer, for example) if the patch is on the positive side of the hyperplane, or a negative patch (negative for cancer, for example) if the patch is on the negative side of the hyperplane, as shown in FIGS. 9A-9B. Once step 511 is complete, each test patch 323 is marked as either positive or negative.

Once the classification of step 511 is complete, the system proceeds to step 513, the grouping step. In step 513, the test patches 323 that have been determined to be positive are grouped with other neighboring positive patches. Similarly, the test patches 323 that have been determined to be negative are grouped with other neighboring negative patches. Step 513 is described in further detail below, with reference to FIG. 5D.

In general, the process through generation of the convex hulls is as follows: (1) build patch grid map based on two class SVM (positive is 1, negative is 0); (2) convolve this map with adjacency kernel; (3) create primary blobs. Inside each blob, each patch must have a score of at least 7.5 and all patches being connected; (4) create supporting blobs, inside each supporting blob, each patch must have a score of at least 4.0 and all patches being connected; and (5) build convex hull for each of primary and supporting blobs.

At step 513A, the grouping engine 317 determines a probability score by analyzing each test patch 323 and its neighboring patches. Specifically, a score is determined as follows: start from 0 and add 2 if the patch itself has been classified as the relevant class (positive or negative), add 1 for each patch directly above, below, to the left, and to the right have been classified as the same class (i.e., positive or negative), and add 0.5 for each neighboring corner patch classified as the same class.

Figure 10A:
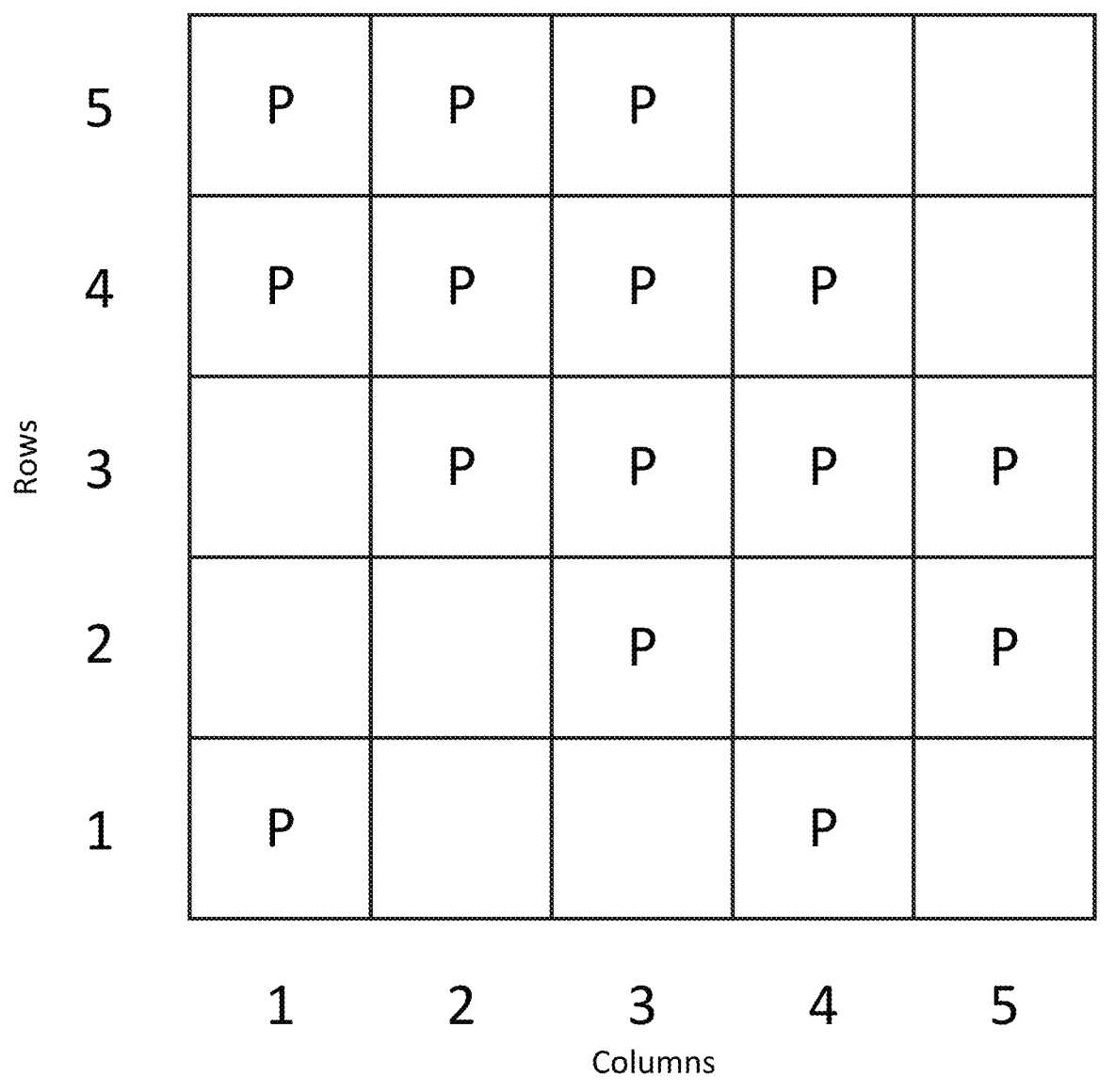

For example, FIG. 10A shows a representative portion of test patches 323. The P in certain patches indicates that the two-class SVM 315 has determined that the patch is positive. Analyzing, for example, patch(2, 4) (column 2, row 4), this patch would have a probability score of 7.5. We add 2 because the patch itself (2, 4) has been determined to be positive by the two-class SVM 315. We add 1 for each of the patches on top, bottom, left and right of the relevant patch (1, 4), (2, 5), (3, 4), and (2, 3). And we add 0.5 for each of the 3 neighboring corner patches (1, 5), (3, 5), and (3, 3). Since (1, 3) is not indicated as positive, 0.5 is not added to the probability score for that patch. Thus, its probability score becomes 2+4+1.5=7.5.

As another example, patch (4, 2) would have a score of 5.0 (1.0 for each of patches (3, 2), (4, 3), (5, 2), and (4, 1) and 0.5 each for corner patches (3, 3) and (5, 3)).

According to step 513B, once the above process has been performed for all test patches 323, any patches with a probability score of 7.5 or above are considered primary blobs and any patches with a probability score of 4.0 and above are considered supporting areas (these numbers are just example and different numbers may be used). More specifically, two binary maps are generated: primary and supporting. The primary binary map includes only patches with a score of 7.5 and above and the supporting binary map includes only patches with a score of 4.0 and above.

In step 513C, the grouping engine 317 generates a convex hull, line string, and point for all primary blobs and assigns a probability score of 7.5 (or the highest score of any patch within the convex hull) for all patches within the convex hull.

Figure 5D:
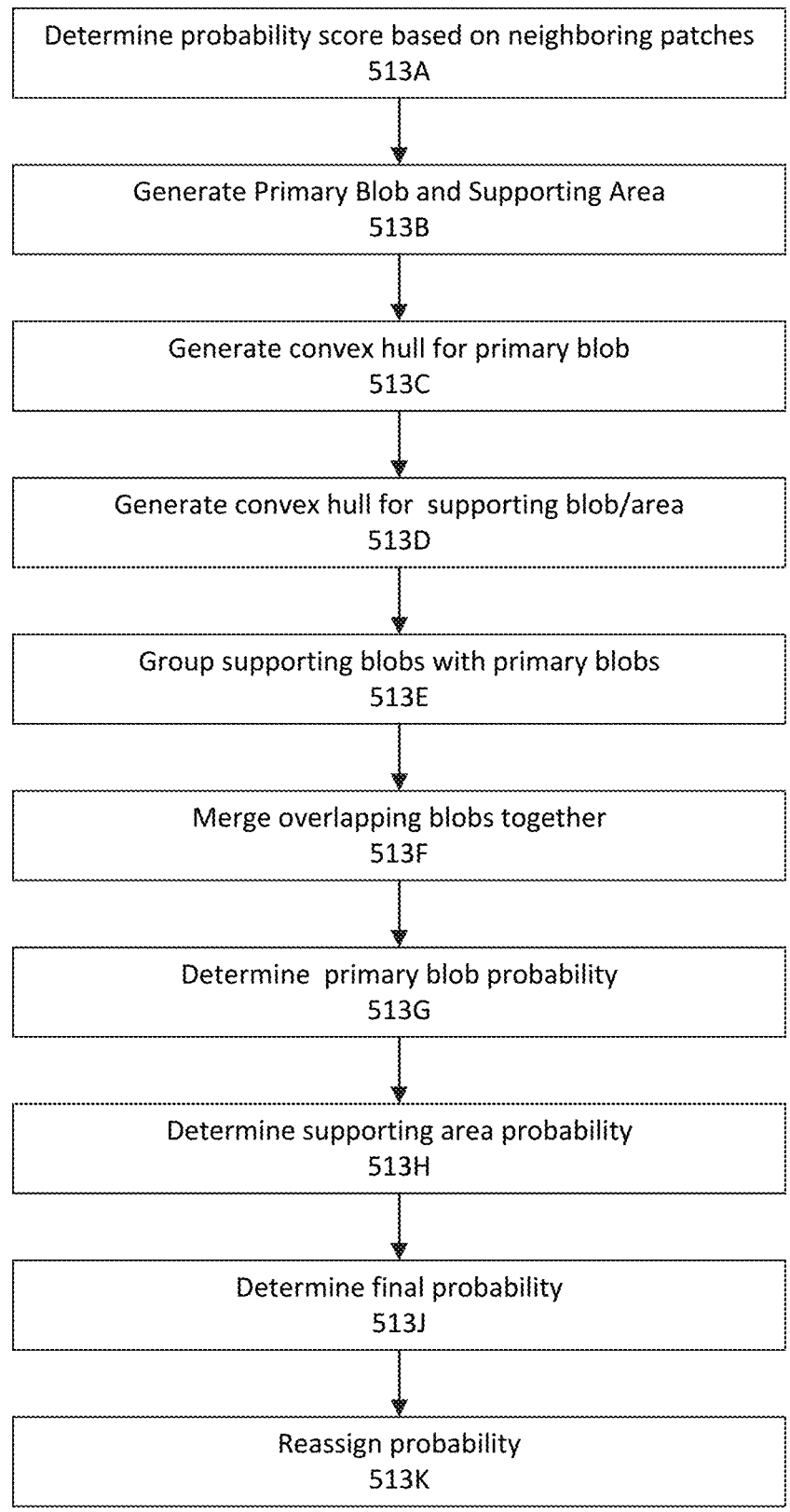
Figure 10B:
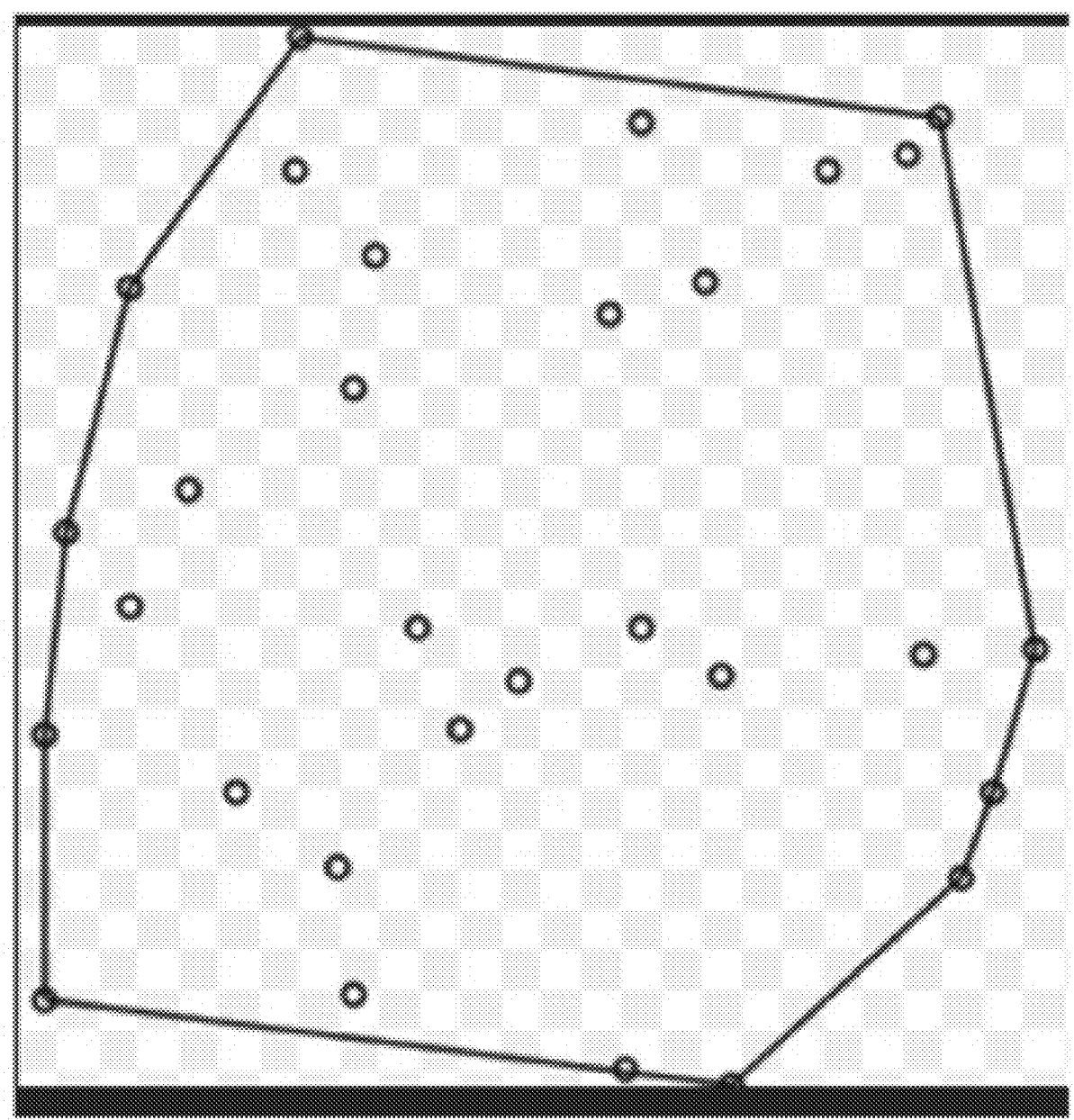
FIG. 10B illustrates a diagram showing a convex hull around a region of interest generated by an electronic device that implements one or more aspects of an embodiment of the invention.

FIG. 10B illustrates a generated convex hull around multiple positive patches (or negative patches, as the case may be. The process of FIG. 5D is performed for positive patches and then for negative patches).

In step 513D, the grouping engine 317 generates a convex hull, line string, and point for supporting blobs and assigns a probability score of 4.0 (or the highest score of any patch within the convex hull) for all patches within the convex hull.

In step 513E, the grouping engine 317 merges supporting blobs with primary blobs if the primary blobs and supporting blobs have overlapping geometry. The overlapping geometry determination is made if one of the vertices of one convex hull (for example, a primary blob convex hull) is inside the other convex hull (for example, a supporting blob/area convex hull). That it is, for each vertex in one hull, the system determined if it is inside any other convex hull. If no vertex is inside another convex hull, the two convex hulls do not overlap.

In step 513F, if the convex hull, line string or point intersect, the grouping engine 317 groups the convex hulls together using largest overlapping criteria.

In step 513G, the probability of each of the primary blobs is determined as follows: $Probability_{primary}=k*primary\_patch\_count$, where k is a constant such as 0.1, 0.2, 0.3, 0.4, or 0.5 and primary_patch_count is the number of patches in a particular primary blob. The constant k may be set by the user or be predetermined. For example, if k is 0.1 and the primary_patch_count is 13, the probability is then 0.1*13=1.3. The purpose of the above calculation is to take into account that blobs that have been identified as likely containing positive patches that include a larger number of patches are more likely to be positive than blobs with a lower number of patches.

In step 513H, the probability score of each of the supporting areas/blobs being merged into a primary blob is determined as follows: $Probability_{supporting}=k*supporting\_patch\_count/j$, where k is a constant such as 0.1, 0.2, 0.3, 0.4, or 0.5, supporting_patch_count is the patch count of the number of patches in all supporting blobs being merged into a particular primary blob, and j is a constant such as 50, 60, 70, 80, 90, 100, 110, 120, 130, 140, or 150. For example, if k is 0.5, the supporting_patch_count is 300, and j is 100, the probability is then 0.5*300/100=1.5. Finally, if $Probability_{supporting}>=k$ or another constant, the $Probability_{supporting}$ is set to k. For example, in the above example, since Probability supporting was determined to be 1.5, $Probability_{supporting}$ would then be set to the value of k, 0.5, In step 513J, the final probability of the primary blob and the supporting areas/blobs merged into the primary blob is determined as follows: $Probability_{final}=Probability_{primary}+Probability_{supporting}$. For example, if $Probability_{primary}$ is 0.7 and $Probability_{supporting}$ is 0.5, the final probability is 1.2. However, if the final probability is larger than 1.0, the final probability is then set to 1.0. Thus, in the above example, the final probability would be set to 1.0.

Figure 11I:

In step 513K, the grouping engine 317 uses the final grouped convex hulls to reassign the probability to the largest score of any of the convex hulls within the group. The scores of the convex hulls are then stored in regions of interest 321 and, for any convex hull above a threshold such as 1.0, such convex hulls are shown in green in FIGS. 11A-11B and 11G-H to indicate a high likelihood of either positive or negative patches. For example, green may indicate a high likelihood of positive patches. Embodiments of the present invention may be used to indicate a high likelihood of positive patches of various characteristics of the sample/image. For example, in FIGS. 11A-11B and 11G-11H, the green indicates a high likelihood of positive patches of cancer, whereas the green in FIG. 11I indicates a high likelihood of lymphocytes.

A region of interest (ROI) 321 (which may include multiple regions) may then be generated based on the output from step 513K. The regions of interest 321 may include a tissue mask such as a microdissection mask, which may be used in conducting a laser microdissection in order to excise a target ROI for further processing. Only certain ROIs may be used as a microdissection mask based on the size of the ROI and the quality of the ROI. That is, certain ROIs may not be suitable for microdissection.

Embodiments described herein implement few-shot learning in combination with a pathologist's input to more efficiently and quickly generate classification of tissue regions of interest in a sample. A pathologist no longer must manually outline all regions of interest in an image. Rather, a system using the few shot learning techniques described herein helps accelerate the pathologist's work by at least partially automating the process of identifying regions of interest. In another embodiment, output of the disclosed embodiments is used as training data for training a deep learning network (such as CNN 329 shown in FIG. 3) or other machine-learning system that requires large amounts of training data. This allows training data to be generated more efficiently.

While certain illustrative embodiments are described herein, it should be understood that those embodiments are presented by way of example only, and not limitation. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

What is claimed is:

1. A computer implemented method of generating at least one shape of a region of interest in a digital image, the method comprising:
   obtaining, by an image processing engine, access to a digital tissue image of a biological sample;
   tiling, by the image processing engine, the digital tissue image into a collection of image patches;
   obtaining, by the image processing engine, a plurality of features from each patch in the collection of image patches, the plurality of features defining a patch feature vector in a multidimensional feature space including the plurality of features as dimensions;
   determining, by the image processing engine, a user selection of a user selected subset of patches in the collection of image patches, wherein the user selection further includes a selection, prior to selection of the subset of patches in the collection of image patches, of whether the user selected subset of patches are positive or negative patches;
   classifying, by applying a trained classifier to patch vectors of other patches in the collection of patches, the other patches as belonging or not belonging to a same class of interest as the user selected subset of patches; and identifying one or more regions of interest based at least in part on the results of the classifying.

2. The method of claim 1, wherein the step of tiling the digital tissue image includes creating image patches that are of a uniform size and a uniform shape.

3. The method of claim 2, wherein the image patches of uniform size and uniform shape include square patches of less than or equal to 1,000 pixels by 1,000 pixels.

4. The method of claim 3, wherein the square patches are less than or equal to 400 pixels by 400 pixels.

5. The method of claim 3, wherein the square patches are less than or equal to 256 pixels by 256 pixels.

6. The method of claim 1, wherein the step of tiling the digital tissue image includes creating image patches that are of non-uniform size and shape.

7. The method of claim 1, wherein the collection of image patches includes non-overlapping patches.

8. The method of claim 1, wherein the trained classifier includes a support vector machine.

9. The method of claim 8, wherein the support vector machine includes a two-class support vector machine.

10. The method of claim 1, wherein the trained classifier comprises a support vector machine and training patches used to train the support vector machine are generated by a second support vector machine.

11. The method of claim 10, wherein the second support vector machine is a one-class support vector machine that is trained by training patches comprising the user selected subset of patches.

12. The method of claim 10, wherein the support vector machine is a two-class support vector machine and the second support vector machine is a one-class support vector machine that is trained by training patches comprising the user selected subset of patches.

13. The method of claim 1, wherein obtaining the features comprises submitting each patch to a trained image processing neural network that executes feature extraction processing, the feature extraction processing having been trained on images of a variety of known objects.

14. The method of claim 13, wherein the neural network is a convolutional neural network.

15. The method of claim 13, wherein the neural network has been trained on at least 1,000,000 images and the variety of known objects comprises objects belonging to at least 1,000 different classes of known objects.

16. The method of claim 13, wherein a majority of the known objects are not digital tissue images of biological samples.

17. The method of claim 15, wherein a majority of the known objects are not digital tissue images of biological samples.

18. The method of claim 13, wherein all of the known objects are not digital tissue images of biological samples.

19. The method of claim 13, wherein all of the known objects are not in the same class of interest as the user selected subset of patches.

20. The method of claim 1, further comprising causing a computing device to render the region of interest shapes on a display.

21. The method of claim 1, wherein the region of interest shapes includes at least one tissue mask.

22. The method of claim 21, wherein the at least one tissue mask comprises a microdissection mask.

23. The method of claim 1, wherein the class of interest comprises at least one cancer class.

24. The method of claim 23, wherein the at least one cancer class includes one of the following types of cancer: breast cancer, bladder cancer, brain cancer, lung cancer, pancreatic cancer, skin cancer, colorectal cancer, prostate cancer, stomach cancer, liver cancer, cervical cancer, esophageal cancer, leukemia, non-hodgkin lymphoma, kidney cancer, uterine cancer, bile duct cancer, bone cancer, ovarian cancer, gallbladder cancer, gastrointestinal cancer, oral cancer, throat cancer, ocular cancer, pelvic cancer, spinal cancer, testicular cancer, vaginal cancer, vulvar cancer, or thyroid cancer.

25. The method of claim 1, wherein the class of interest comprises at least one of the following types of tissue: abnormal tissue, benign tissue, malignant tissue, bone tissue, skin tissue, nerve tissue, interstitial tissue, muscle tissue, connective tissue, scar tissue, lymphoid tissue, fat, epithelial tissue, nervous tissue, or blood vessels.

26. The method of claim 1, wherein the digital tissue image comprises a slide image of a tissue sample slide.

27. The method of claim 26, wherein the slide image comprises a digital histopathology image.

28. The method of claim 26, wherein the slide image includes biological sample metadata comprising digital information associated with at least one of the following: a tissue type, a tissue donor, a scanner, a stain, a staining technique, an identifier of a preparer, an image size, a sample identifier, a tracking identifier, a version number, a file type, an image date, a symptom, a diagnosis, an identifying information of treating physician, a medical history of the tissue donor, a demographic information of the tissue donor, a medical history of family of the tissue donor, or a species of the tissue donor.

29. An apparatus for generating at least one shape of a region of interest in a digital image, the apparatus comprising:
  a non-transitory, computer readable memory storing software instructions; and
  a processor coupled with the computer readable memory, and, upon execution of the software instructions, is configurable to:
  obtain access to a digital tissue image of a biological sample;
  tile the digital tissue image into a collection of image patches;
  obtain a plurality of features from each patch in the collection of image patches, the plurality of features defining a patch feature vector in a multidimensional feature space including the plurality of features as dimensions;
  determine a user selection of a user selected subset of patches in the collection of image patches, wherein the user selection further includes a selection, prior to selection of the subset of patches in the collection of image patches, of whether the user selected subset of patches are positive or negative patches;
  classify, by applying a trained classifier to patch vectors of other patches in the collection of patches, the other patches as belonging or not belonging to a same class of interest as the user selected subset of patches; and
  identify one or more regions of interest based at least in part on the results of the classifying.

30. A computer implemented method of generating training data to train a machine learning system, the method comprising:
  obtaining, by an image processing engine, access to a digital tissue image of a biological sample;
  tiling, by the image processing engine, the digital tissue image into a collection of image patches;

obtaining, by the image processing engine, a plurality of features from each patch in the collection of image patches, the plurality of features defining a patch feature vector in a multidimensional feature space including the plurality of features as dimensions;

determining, by the image processing engine, a user selection of a user selected subset of patches in the collection of image patches, wherein the user selection further includes a selection, prior to selection of the subset of patches in the collection of image patches, of whether the user selected subset of patches are positive or negative patches;

classifying, by applying a trained generic classifier to patch vectors of other patches in the collection of patches, the other patches as belonging or not belonging to a same class of interest as the user selected subset of patches; and generating, by the image processing engine, training data for the machine learning system based on the classifying of the user-selected and the other patches in the collection of patches.

* * * * *